US008658134B2

(12) United States Patent
Chirila et al.

(10) Patent No.: US 8,658,134 B2
(45) Date of Patent: Feb. 25, 2014

(54) FIBROBLAST GROWTH PATTERNS FOR DIAGNOSIS OF ALZHEIMER'S DISEASE

(75) Inventors: Florin Valentin Chirila, Morgantown, WV (US); Tapan Kumar Khan, Morgantown, WV (US); Daniel L. Alkon, Bethesda, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 0 days.

(21) Appl. No.: 12/896,862

(22) Filed: Oct. 2, 2010

(65) Prior Publication Data
US 2011/0136144 A1 Jun. 9, 2011

Related U.S. Application Data

(60) Provisional application No. 61/248,368, filed on Oct. 2, 2009, provisional application No. 61/344,045, filed on May 13, 2010, provisional application No. 61/362,518, filed on Jul. 8, 2010, provisional application No. 61/365,545, filed on Jul. 19, 2010.

(51) Int. Cl.
G01N 33/483 (2006.01)
C12N 5/07 (2010.01)

(52) U.S. Cl.
USPC ............... 424/9.1; 435/378; 702/19; 702/21

(58) Field of Classification Search
None
See application file for complete search history.

(56) References Cited

U.S. PATENT DOCUMENTS

| | | | |
|---|---|---|---|
| 5,242,932 A | 9/1993 | Gandy et al. | |
| 5,385,915 A | 1/1995 | Buxbaum et al. | |
| 6,077,686 A | 6/2000 | Der et al. | |
| 6,080,582 A | 6/2000 | Alkon et al. | |
| 6,080,784 A | 6/2000 | Driedger et al. | |
| 6,107,050 A | 8/2000 | Alkon et al. | |
| 7,595,167 B2 | 9/2009 | Khan et al. | |
| 2001/0051344 A1 | 12/2001 | Shalon et al. | |
| 2003/0108956 A1 | 6/2003 | Alkon et al. | |
| 2003/0153014 A1 | 8/2003 | Shen et al. | |
| 2004/0014678 A1 | 1/2004 | Favit et al. | |
| 2004/0086905 A1 | 5/2004 | Das et al. | |
| 2005/0059092 A1 | 3/2005 | Zhao et al. | |
| 2005/0075393 A1 | 4/2005 | Nishizaki et al. | |
| 2007/0082366 A1 | 4/2007 | Khan et al. | |
| 2009/0029873 A1 | 1/2009 | Khan et al. | |

FOREIGN PATENT DOCUMENTS

| | | |
|---|---|---|
| EP | 0 735 370 | 10/1996 |
| JP | 06-279311 | 10/1994 |
| JP | 10-090263 | 4/1998 |
| WO | WO 93/11231 A | 6/1993 |
| WO | WO 00/20867 | 4/2000 |
| WO | WO 00/70099 | 11/2000 |
| WO | WO 01/69244 A2 | 9/2001 |
| WO | WO 02/10768 A2 | 2/2002 |
| WO | WO 02/50013 | 6/2002 |
| WO | WO 02/067764 | 9/2002 |
| WO | WO 03/102016 | 12/2003 |
| WO | WO 2004/083241 A2 | 9/2004 |
| WO | WO 2006/050475 | 5/2006 |
| WO | WO 2006/054979 | 5/2006 |
| WO | WO 2007/043998 | 4/2007 |
| WO | WO 2007/044094 A1 | 4/2007 |
| WO | WO 2007/047029 | 4/2007 |
| WO | WO 2007/149985 A2 | 12/2007 |
| WO | WO 2008/100449 | 8/2008 |
| WO | WO 2008/148115 A1 | 12/2008 |

OTHER PUBLICATIONS

Balin et al., Normal replicative lifespan of Alzheimer skin fibroblasts, Neurobiol Aging, 9:195-198, 1988.*
Tesco et al., Growth properties of familial Alzheimer skin fibroblasts during in vitro aging, Exp Gerontology, 28(1):51-8, 1993.*
Carmeliet et al., Growth properties and in vitro life span of Alzheimer disease and Down syndrome fibroblasts-a blind study, Mech. Aging Dev. 53: 17-33, 1990.*
Kleinman et al., Use of extracellular matrix components for cell culture, Analytical Biochemistry, 166(1):1-13, 1987.*
Furukawa et al., Formation of Human Fibroblast Aggregates (Spheroids) by Rotational Culture, Cell Transplantation, 10(4-5):441-445, 2001.*
Laurent-Matha et al., Catalytically inactive human cathepsin D triggers fibroblast invasive growth, Journal of Cell Biol., 168(3):489-499, 2005.*
Urbanelli et al., Cathepsin D expression is decreased in Alzheimer's disease fibroblasts, Neurobiology of Aging, 29:12-22, 2008.*
Matrigel fact sheet, BD catalog, 2008.*
Cornforth et al., "Automated classification reveals morphological factors associated with dementia," Applied Soft Computing, vol. 8, 2008, pp. 182-190.
International Search Report and Written Opinion issued in PCT/US2010/051236 on Mar. 2, 2011.
Solerte et al., "Hemorheological changes and overproduction of cytokines from immune cells in mild to moderate dementia of the Alzheimer's type: adverse effects on cerebromicrovascular system," Neurobiology of Aging, vol. 21, No. 2, Mar. 1, 2000, pp. 271-287.

(Continued)

Primary Examiner — Daniel E Kolker
Assistant Examiner — Stacey N MacFarlane
(74) Attorney, Agent, or Firm — Finnegan, Henderson, Farabow, Garrett & Dunner LLP

(57) ABSTRACT

Methods of diagnosing Alzheimer's disease are provided. At least five methods of diagnostic measurements are presented: Method 1: Integrated score; Method 2: Average aggregate area per number of aggregates; Method 3: Cell migration analysis; Method 4; Fractal analysis; Method 5: Lacunarity Analysis. In certain embodiments, a sample of a subject's skin provides a network of fibroblasts that is imaged and a fractal dimension of the image is calculated. The fractal dimension can be compared to an aged-matched control (non-Alzheimer's) database to determine if the subject has Alzheimer's disease. The network of fibroblasts may be cultured in a matrix, for example in a protein mixture.

30 Claims, 20 Drawing Sheets

(56) References Cited

OTHER PUBLICATIONS

Alkon et al., Protein Synthesis Required for Long-Term Memory is Induced by PKC Activation on Days Before Associative Learning, Proc. Natl. Acad. Sci. USA, 102(45):16432-16437 (2005).

Anderson et al., "Oxidative Signalling and Inflammatory Pathways in Alzheimer's Disease," Biochem. Soc. Symp., 67:141-149 (2001).

Baker et al., "System Manifestation of Alzheimer's Disease," Age, 11:60-65 (1988).

Barrow et al., "Functional Phenotype in Transgenic Mice Expressing Mutant Human Presenilin-1," Neurobiology of Disease 7: 119-126 (2000).

Bassa BV, et al.,."Lysophosphatidylcholine Activates Mesangial Cell PKC and MAP Kinase by PLCy-1 and Tyrosine Kinase-Ras Pathways," Am J Physiol, 277:F328-2337 (1999).

Bernier et al., "Bradykinin-regulated Interactions of the Mitogen-activated Protein Kinase Pathway with the Endothelial Nitric-oxide Synthase," J. Biol. Chem., 275(39):30707-30715 (2000).

Berridge, "Inositol Triphosphate and Diacylglycerol as Second Messengers," Biochem J., 220:345-360 (1984).

Biernat et al., "Phosphorylation of Ser 262 Strongly Reduces Binding of Tau to Microtubules: Distinction between PHF-like Immunoreactivity and Microtubule Binding," Neuron, 11:153-163 (1993).

Blanchard et al., "Hyperphosphorylation of Human TAU by Brain Kinase PK40erk beyond Phosphorylation by cAMP-dependent PKA: Relation to Alzheimer's Disease." Biochem. Biophys. Res. Commun., 200(1):187-194 (1994).

Bockman et al., "Kinins and Kinin Receptors: Importance for the Activation of Leukocytes," Journal of Leukocyte Biology, 68:587-592 (Nov. 2000).

Bondy et al., "The PHA-Induced Calcium Signal in Lymphocytes is Altered After Blockade of K+-Channels in Alzheimer's Disease," J. Psychiat. Res., 30(3):217-227 (1996).

Brooks et al., "Gene Expression Profiles of Metabolic Enzyme Transcripts in Alzheimer's Disease," Brain Res, 1127(1):127-135 (2007).

Burke et al., "Update on Alzheimer's Disease: Promising advances in Detection and Treatment," Postgraduate Medicine, 106(5):85-96 (1999).

Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).

Caporaso et al., "Protein Phosphorylation Regulates Secretion of Alzheimer B/A4 Amyloid Precursor Protein," Proc. Natl. Acad. Sci. USA, 89:3055-3059 (Apr. 1992).

Chapman et al., "Genes, Models and Alzheimer's Disease," Trends in Genetics, 17(5):254-261 (May 2001).

Connolly, G.P., "Fibroblast Models of Neurological Disorders: Fluorescence Measurement Studies", Trends Pharmacol. Sci. 19, 171-177 (1998).

Cruzblanca et al., "Bradykinin Inhibits M Current via Phospholipase C and $Ca^{2+}$ Release from $IP_3$-sensitive $Ca^{2+}$ Stores in Rat Sympathetic Neurons," Proc. Natl. Acad. Sci. USA, 95:7151-7156 (Jun. 1998).

Dunckley et al., Gene Expression Correlates of Neurofibrillary Tangles in Alzheimer's Disease, Neurobiol Aging, 27(10):1359-1371 (2006).

Ekinci et al., "Hyperactivation of Mitogen-Activated Protein Kinase Increases Phospho-Tau Immunoreactivity Within Human Neuroblastoma: Additive and Synergistic Influence of Alteration of Additional Kinase Activities," Cell Mol. Neurobiol., 19(2):249-260 (1999).

El-Dahr et al., "Bradykinin Stimulates the ERK-Elk-1-Fos/AP-1 Pathway in mesangial Cells," American Journal of Psychology, 275(3 Part w):F343-F352 (Sep. 1998).

English-language Translation for JP10-90263 dated Apnl 10, 1998.

English-language Translation for JP 6-279311 dated Jun. 2008.

Etcheberrigaray et al., "Ionic and Signal Transduction Alterations in Alzheimer's Disease," Molecular Neurobiology, 20:93-109 (1999).

Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).

Etcheberrigaray et al., "Calcium Responses in Fibroblasts from Asymptomatic Members of Alzheimer's Disease Families," Neurobiol. of Disease., 5:37-45 (1998).

Etcheberrigaray et al., "Potassium Channel Dysfunction in Fibroblasts Identifies Patients with Alzheimer Disease," Proc. Natl. Acad. Sci. USA, 90:8209-8213 (Sep. 1993).

Etcheberrigaray et al., "Therapeutic effects of PKC activators in Alzheimer's disease transgenic mice", PNAS, 101(30):11141-11146 (2004).

Etcheberrigary et al., "Molecular Mechanisms of Memory and the Pathophysiology of Alzheimer's Disease," Ann NY Acad Sci., 747:245-55 (1994).

European Search Report for EP 02 72 3236 dated Mar. 24, 2004.

Extended European Search Report issued on EP 08 02 0258 dated Jan. 30, 2009.

Extended European Search Report issued on EP 10 01 1288, dated Mar. 25, 2011.

Extended European Search Report issued on EP 10 01 1289 dated Mar. 23, 2011.

Extended European Search Report issued on EP 10 01 2836, dated Mar. 25, 2011.

Extended European Search Report issued on EP 10 011 290, dated Mar. 23, 2011.

Fan et al., "Arachidonic Acid and Related Methyl Ester Mediate Protein Kinase C Activation in Intact Platelets Through the Arachidonate Metabolism Pathways," Biochemical and Biophysical Research Communications, 169(3):933-940 (Jun. 29, 1990).

Favit et al., "Alzheimer's-specific effects of soluble β-amyloid on protein kinase C-and -γ degradation in human fibroblasts", Cell Biology, 95:5562-5567 (1998).

Final Office Action mailed Sep. 13, 2011, in U.S. Appl. No. 11/660,868.

Final Office Action mailed Oct. 11, 2011, in U.S. Appl. No. 12/083,056.

Frey et al. "Problems Associated with Biological Markers of Alzheimer's Disease," Neurochemical Research, 30(12):1501-1510 (Dec. 2005).

Gasparini et al., "Stimulation of β-Amyloid Precursor Trafficking by Insulin Reduces Intraneuronal β-Amyloid and Requires Mitogen-Activated Protein Kinase Signaling," The Journal of Neuroscience, 21(8):2561-2570 (Apr. 15, 2001).

Gebreyesus et al., "Bradykinin Elevates Tyrosine Hydroxylase and Dopamine Beta-Hydroxylase mRNA levels in PC12 Cells," Brain Research, 608(2):345-348 (1993).

Gibson et al., "Calcium stores in cultured fibroblasts and their changes with Alzheimer's disease," Biochimica et Biophysica Acta, 1316:71-77 (1996).

Gillespie et al., "Secretory Processing of the Alzheimer Amyloid B/A4 Protein Precursor is Increased by Protein Phosphorylation," Biochemical and Biophysical Research Communications, 187(3):1285-1290 (1992).

Govoni et al., "Cytosol Protein Kinase C Downregulation in Fibroblasts from Alzheimer's Disease Patients," Neurology, 43:2581-2586 (1993).

Grant et al., "Phosphorylation of Mitogen-Activated Protein Kinase is Altered in Neuroectodermal Cells Overexpressing the Human Amyloid Precursor Protein 751 Isoform," Molecular Brain Research., 72:115-120 (1999).

Greenberg et al., "Secreted Beta-amyloid Precursor Protein Stimulates Mitogen-activated Protein Kinase and Enhances Tau Phosphorylation," Proc Natl Acad Sci USA, 91:7104-7108 (1994).

Growdon et al., "Biomarkers of Alzheimer Disease", Arch Neurol., 56(3): 281-283, (1999).

Haug et al., "Decreased Inositol (1 ,4,5)-Trisphosphate Receptor Levels in Alzheimer's Disease Cerebral Cortex: Selectivity of Changes and Possible Correlation to Pathological Severity," Neurodegeneration, 5:169-176 (1996).

Hetman et al., "Role of Extracellular Signal Regulated Kinases 1 and 2 in Neuronal Survival," Eur. J. Biochem, 271:2050-2055 (2004).

(56) References Cited

OTHER PUBLICATIONS

Hirashima et al., "Calcium Responses in Human Fibroblasts: A Diagnostic Molecular Profile for Alzheimer's Disease," Neurology of Aging, 17(4):549-555 (1996).
Hogervorst et al., "The Validity and Reliability of 6 Sets of Clinical Criteria to Classify Alzheimer's Disease and Vascular Dementia in Cases confirmed Post-Mortem: Added Value of a Decision Tree Approach," Dement Geriatr Coqn Disord 16:170-180 (2003).
Hongpaisan et al., "A structural basis for enhancement of long-term associative memory in single dendritic spines regulated by PKC", Proc. Natl. Acad. Sci .USA, 104(49):19571-19576 (Dec. 4, 2007).
Huang et al., "Increased Inositol 1,4, 5-Trisphosphate Accumulation Correlates With an Up-Regulation of Bradykinin Receptors in Alzheimer's Disease," Journal of Neurochemistry, 64(2):761-766 (Feb. 1995).
Huang et al., "Inositol Phosphates and Intracellular Calcium after Bradykinin Stimulation in Fibroblasts from Young, Normal Aged and Alzheimer Donors," Neurobiology of Aging, US, 12(5):469-473 (Sep. 1991).
Huynh et al., "Reduced Protein Kinase C Immunoreactivity and Altered Protein Phosphorylation in Alzheimer's Disease Fibroblasts," Arch Neurol 46:1195-1198 (1989).
Hyman et al.,, "Extracellular Signal-Regulated Kinase (MAP Kinase) Immunoreactivity in the Rhesus Monkey Brain." Neuroscience Letters, 166:113-116 (1994).
International Preliminary Report on Patentability and Written Opinion for PCT/2005/036014 dated Apr. 24, 2008.
International Preliminary Report on Patentability and Written Opinion for PCT/2006/022156 dated Apr. 24, 2008.
International Preliminary Report on Patentability and Written Opinion for PCT/US2006/037186 dated Apr. 16, 2008.
International Search Report and Written Opinion for PCT/US2006/037186 dated Apr. 11, 2007.
International Search Report and Written Opinion on PCT/US2005/036014 dated Oct. 19, 2006.
International Search Report and Written Opinion on PCT/US2006/022156 dated Feb. 8, 2007.
International Search Report issued on PCT/US2005/036014, mailed Oct. 19, 2006.
International Search Report issued on PCT/US2006/022156, mailed Feb. 8, 2007.
International Search Report issued on PCT/US2009/002120, mailed Sep. 25, 2009.
Irizarry et al., "Biomarkers of Alzheimer Disease in Plasma," The Journal of the American Society for Experimental NeuroTherapeutics, 1:226-234 (Apr. 2004).
Ito et al., "Internal $Ca^{2+}$ Mobilization is Altered in Fibroblasts from Patients with Alzheimer Disease." Proc Natl Acad Sci USA, 91:534-538 (1994).
Jin et al., "Changes in Protein Kinases in Brain Aging and Alzheimer's Disease," Drugs & Aging, 6(2):136-149 (1995).
Kanno et al., "The Linoleic Acid Derivative DCP-LA Selectively Activates PKC-ε, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ε", Dept. of Physiology, Hyogo College of Med., Hyogo, Japan, Bulletin of the Japanese Society for Neurochemistry, 45(2-3): p. 552 (2006).
Khan et al., "A Cellular Model of Alzheimer's Disease Therapeutic Efficacy: PKC Activation Reverses A Beta-Induced Biomarker Abnormality on Cultured Fibroblasts," Neurobiology of Disease, 34(2): 332-339 (May 2009).
Khan et al., "An Internally Controlled Peripheral Biomarker for Alzheimer's Disease: Erk1 and Erk2 responses to the Inflammatory Signal Bradykinin," PNAS, 103(35): 13203-13207 (Aug. 29, 2006).
Kilpatrick et al., "Regulation of TNF Mediated Antiapoptoptic Signaling in Human Neutrophils: Role of -PKC and ERK1/2," Journal of Leukocyte Biology, 80:1512-1521 (Dec. 2006).
Kurumatani et al., "Loss of Inositol 1,4,5-trisphosphate Receptor Sites and Decreased PKC Levels Correlate with Staging of Alzheimer's Disease Neurofibrillary Pathology," Brain Research, 796:209-221 (1998).
Laporte et al., "Role of ERK MAP Kinases in Responses of Cultured Human Airway Smooth Muscles Cells to IL-1B." Am. J. Physiol. Lung Cell Mol. Physiol., 277:943-951 (1999).
Leissring et al., "Capacitative Calcium Entry Deficits and Elevated Luminal Calcium Content in Mutant Presenilin-1 Knockin Mice," The Journal of Cell Biology, 149:793-797 (2000).
Leissring et al., "Presenilin-2 Mutations Modulate Amplitude and Kinetics of Inositol 1,4,5-Trisphosphate-mediated Calcium Signals," The Journal of Biological Chemistry, 274(46):32535-32538 (Nov. 12, 1999).
Liang et al., "Altered Neuronal Gene Expression in Brain Regions Differentially affected by Alzheimer's Disease: A reference Data Chart," Physiol Genomics, 33:240-256 (2008).
Loring et al., "A Gene Expression Profile of Alzheimer's Disease," DNA and Cell Biology, 20(11):683-695 (2001).
Lu et al., $P44^{mpk}$ MAP Kinase Induces Alzheimer Type Alterations in Tau Function and in Primary Hippocampal Neurons, J. Neurosci. Res., 35:439-444 (1993).
Luigi et al., "Inflammatory Markers in Alzheimer's Disease and Multi-Infarct Dementia," Mechanisms of Ageing and Development, 122:1985-1995 (2001).
Masliah et al., "Differential Involvement of Protein Kinase C Isozymes in Alzheimer's Disease," The Journal of Neuroscience, 10(7): 2113-2124 (Jul. 1990).
Masliah, "Protein Kinase C Alteration is an Early Biochemical Marker in Alzheimer's Disease," The Journal of Neuroscience, 11(9): 2759-2767 (1991).
Mattson et al., "Presenilin-1 Mutation Increases Neuronal Vulnerability to Focal Ischemia In Vivo and to Hypoxia and Glucose Deprivation in Cell Culture: Involvement of Perturbed Calcium Homeostasis," The Journal of Neuroscience, 20(4):1358-1364 (Feb. 15, 2000).
McDonald et al., "β-Amyloid Fibrils Activate Parallel Mitogen-Activated Protein Kinase Pathways in Microglia and THP1 Monocytes," J Neurosci, 18(12):4451-4460 (1998).
Nagasaka et al., "A Unique Gene Expression Signature Discriminates Familial Alzheimer's Disease Mutation Carriers from their Wild-type Siblings," Proc. Natl. Acad. Sci., 102(41):14854-14859 (2005).
Nagata et al., "FR236924, a Newly Synthesized Derivative of Linoleic Acid, Ameliorates Memory Deficits in Rats Intraventricularly Injected with Amyloid-Beta Peptide." Jpn. J. Physiol. 53,Suppl. 53(319): S216 (2003).
Nagata et al., "The Newly Synthesized Linoleic Acid Derivative CP-LA Ameliorates Memory Deficits in Animal models Treated with Amyloid-β Peptide and Scopolamine", Psychogeriatrics, 5:122-126 (2003).
Neve et al., "Alzheimer's Disease: Dysfunction of a Signalling Pathway Mediated by the Amyloid Precursor Protein?" Biochem. Soc. Symp. 67:37-50, (2001).
Ning et al., "Early Response Gene Signalling in Bryostatin-Stimulated Primary B Chronic Lymphocytic Leukaemia Cells in Vitro," Biochemical Journal, 319(1):59-65 (1996).
NME Digest, Drug News Perspect, 15(10): 666-674 (2002).
Oddo et al., "Temporal Profile of Amyloid-β (AB) Oligomerization in an in Vivo Model of Alzheimer Disease—A Link Between AB and TAU Pathology," Journal of Biological Chemistry, 281(3):1599-1604 (Jan. 20, 2006).
Office Action (Restriction Requirement) mailed Aug. 16, 2011, in U.S. Appl. No. 12/510,707.
Office Action (Restriction Requirement) mailed Dec. 2, 2010, in U.S. Appl. No. 12/083,056.
Office Action (Restriction Requirement) mailed May 23, 2011, in U.S. Appl. No. 12/510,681.
Office Action (Restriction Requirement) mailed Oct. 27, 2010, in U.S. Appl. No. 12/729,042.
Office Action mailed Dec. 21, 2010, in U.S. Appl. No. 11/660,868.
Office Action (Requirement for Restriction) mailed Aug. 12, 2010, in U.S. Appl. No. 11/660,868.
Office Action mailed Apr. 29, 2011, in U.S. Appl. No. 12/083,056.

(56) References Cited

OTHER PUBLICATIONS

Office Action mailed Jun. 7, 2011, in U.S. Appl. No. 12/729,042.
Ohta et al., "Stearic Acid Facilities Hippocampal Neurotransmission by Enhancing nicotinic Ach Receptor Responses via an PKC Pathway," Molecular Brain Research, 119:83-89 (Aug. 27, 2003).
Pascale et al., "Enhanced BK-Induced Calcium Responsiveness in PC12 Cells Expressing the C100 Fragment of the Amyloid Precursor Protein," Brain Res Mol Brain Res, 72:205-213 (1999).
PUB CHEM Compound, XP002550143 (May 27, 2005).
Putney, Jr., "Presenilins, Alzheimer's Disease, and Capacitative Calcium Entry," Neuro, 27:411-412 (2000).
Racchi et al., "Bradykinin-induced amyloid precursor protein secretion: a protein kinase C-independent mechanism that is not altered in fibroblasts from patients with sporadic Alzheimer's disease", Biochem J., 330: 1271-1275 (1998).
Rapoport et al., "PD98059 Prevents Neurite Degeneration Induced by Fibrillar B-Amyloid in Mature Hippocampal Neurons", J. Neurochem., 74:.125-133 (2000).
Reynolds et al., "Phosphorylation Sites on Tau Identified by Nanoelectrospray Mass Spectrometry:Differences in Vitro Between the Mitogen-Activated Protein Kinase ERK2, c-Jun N-Terminal Kinase and P38, and Glycogen Synthase Kinase-3B," J. Neurochem., 74:1587-1595 (2000).
Roux et al., "ERK and p38 MAPK-Activated Protein Kinases: a Family of Protein Kinase with Diverse Biological Functions," Microbiology and Molecular Biology Reviews, 68(2):320-344 (Jun. 2004).
Sato et al., "Elevated Amyloid Beta Protein (1-40) Level Induces CREB Phosphorylation at Serine-133 via p44/42 MAP kinase (Erk1/2)-dependent pathway in rat pheochromocytoma PC12 cells," Biochemical and Biophysical Research Communications, 232(3):637-642(Mar. 27, 1997).
Sheehan et al., "Calcium Homeostasis and Reactive Oxygen Species Production in Cells Transformed by Mitochondria from Individuals with Sporadic Alzheimer's Disease," The Journal of Neuroscience, 17(12):4612-4622 (Jun. 15, 1997).
Sun et al., "Poststroke neuronal rescue and synaptogenesis mediated in vivo by protein kinase C in adult brains", Proc. Natl. Acad. Sci. USA, 105(36): 13620-13625 (Sep. 9, 2008).
Sun et al., "Dual Effects of Bryostatin-1 on Spatial Memory and Depression", Eur. J. Pharmacol., 512: 43-51 (2005).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurobiology of Disease, 3:159-168 (1996).
Thal et al., "The Role of Biomarkers in Clinical Trials for Alzheimer Disease," Alzheimer Dis Assoc Disord, 20(1):6-15 (Jan.-Mar. 2006).
Yaguchi et al., "Effects of Cis-unsaturated Free Fatty Acids on PKC-ϵ Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Yang et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Yoo et al., "Presenilin-Mediated Modulation of Capacitative Calcium Entry," Neuron, 27:561-572 (Sep. 2000).
Youdim et al., "Molecular Basis of Neuroprotective Activities of Rasagiline and the Anti-Alzheimer Drug TV3326 [(N-Propargyl-(3R)Aminoindan-5-YL)-Ethyl Methyl Carbamate]," Cellular and Molecular Neurobiology, 21(6): 555-573 (Dec. 2001).
Young, et al., "Decreased Brain [3H]inositol 1,4,5-trisphosphate Binding in Alzheimer's Disease," Neuroscience Letters, 94:198-202 (1988).
Zhang et al., "Oxidative Stress Differentially Modulates Phosphorylation of ERK, p38 and CREB Induced by NGF or EGF in PC12 Cells." Neurobiology of Aging, 20:271-278 (1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Dysfunction of MAP Kinase signaling in Alzheimer's Disease," Society of Neuroscience, Abstracts 25, 31st Annual Meeting of the Society of Neuroscience, San Diego, CA, USA, 27(1):924, (Nov. 10-15, 2001).
Zhao et al., "MAP Kinase Signaling Cascade Dysfunction Specific to Alzheimer's Disease in Fibroblasts," Neurobiology of Disease, 11(1):116-183 (Oct. 2002).
Bailn et al., "Normal replicative lifespan of Alzheimer skin fibroblasts", Neurobiol Aging, 9: 195-198 (1988).
Becton, Dickenson& Co., BD GentestTM Primary Hepatocytes, 13: 1-14 (2008).
Clark et al. "Evidence that the Bradykinin-induced Activation of Phospholipase D and of the Mitogen-activated Protein Kinase Cascade Involve Different Protein Kinase C. Isoforms," J. Biol. Chem. 270(13):7097-7103 (1995).
Cuenda et al., "Use of Kinase Inhibitors to Dissect Signaling Pathways," Methods in Molecular Biology, Humana Press Inc., Totowa, NJ, Chapter 13, 99: 161-175 (2000).
Est Profile Hs.400740, available at www.ncbi.nlm.nih.gov/UniGene, printed on Aug. 3, 2012, pp. 1-3.
Furukawa et al., "Formation of Human Fibroblast Aggregates (Spheroids) by Rotational Culture", Cell Transplantation, 10: 441-445 (2001).
Johnson et al., "IQGAP1 regulation and roles in cancer", Cellular Signalling, 21: 1471-1478 (2009).
Kleinman et al., "Use of extracellular matrix components for cell culture", Analytical Biochemistry, 166: 1-13 (1987).
Laurent-Matha et al., "Catalytically inactive human cathepsin D triggers fibroblast invasive growth", Journal of Cell Biology, 168(3): 489-499 (Jan. 31, 2005).
Office Action mailed Aug. 24, 2012, in U.S. Appl. No. 12/083,056.
Office Action mailed Sep. 20, 2012, in U.S. Appl. No. 12/729,042.
Office Action mailed Aug. 17, 2012, in U.S. Appl. No. 11/660,868.
Office Action mailed Nov. 15, 2012, in U.S. Appl. No. 12/510,707.
Pasinetti GM., "Use of cDNA Microarray in the Search for Molecular Markers Involved in the Onset of Alzheimer's Disease Dementia", J Neurosci Res., 65(6):471-476, (Aug. 31, 2001).
Shaw et al., "Biomakers of neurodegeneration for diagnosis and monitoring therapeutics," 6: 295-303 (2007).
Urbanelli et al., "Cathepsin D expression is decreased in Alzheimer's disease fibroblasts", Neurobiology of Aging, 29: 12-22 (2008).
Weeraratna et al., "Alterations in immunological and neurological gene expression patterns in Alzheimer's disease tissues", 313, pp. 450-461 (2007).
Zhu et al., "The role of mitogen-activated protein kinase pathways in Alzheimer's disease," Neurosignals, 11(5):270-281 (Sep.-Oct. 2002).
Carmeliet, G. et al. "Growth properties and in vitro life span of Alzheimer disease and Down syndrome fibroblasts. A blind study." *Mech. Ageing Dev.*, 53(1): 17-33 (Mar. 31, 1990), Abstract.
Favit, A. et al. "PKC Isoenzymes are Differentially Affected by Low Concentrations of Soluble Beta-Amyloid Protein in Alzheimer's Disease," *Society for Neuroscience Abstracts*, 23(1-2): 293 (1993), Abstract.
Tesco, G. et al. Growth properties of familial Alzheimer skin fibroblasts during in vitro aging,: *Exp. Gerontol.* 28(1): 51-58 (Jan.-Feb. 1993), Abstract.
Zhao, W. et al. "Impairment of phosphatase 2A contributes to the prolonged MAP kinase phosphorylation in Alzheimer's disease fibroblasts," *Neurobiology of Disease*, 14: 459-469 (2003).

* cited by examiner

INITIAL PREPARATION OF FIBROBLASTS

HUMAN SKIN FIBROBLASTS ARE PLATED

HUMAN SKIN FIBROBLASTS FORM NETWORKS

1. MEASURE FRACTAL DIMENSION AND LACUNARITY

2. EXTRACT SLOPE AND INTERCEPT FROM FRACTAL CURVES

3. EXTRACT AVERAGE LACUNARITY CURVES

FIBROBLAST GROWTH PATTERNS FOR DIAGNOSIS OF ALZHEIMER'S DISEASE

The instant application claims priority to U.S. Provisional Application 61/248,368 filed Oct. 2, 2009 and U.S. Provisional Application 61/344,045 filed May 13, 2010 and U.S. Provisional Application 61/362,518 filed Jul. 8, 2010 and U.S. Provisional Application 61/365,545 filed Jul. 19, 2010, the disclosures of which are hereby incorporated herein in their entireties.

FIELD OF THE INVENTION

The present invention relates to methods to diagnose Alzheimer's disease using fibroblast growth patterns as a biomarker.

BACKGROUND OF THE INVENTION

Alzheimer's disease (AD) is a neurodegenerative disorder characterized by the progressive decline of memory and cognitive functions. It is estimated that over five million Americans are living with this progressive and fatal disease. Alzheimer's destroys brain cells, causing memory loss and problems with thinking and behavior that decrease quality of life. AD has no known cure, but treatments for symptoms can improve the quality of life of the millions of people, and their families, suffering from AD. An early diagnosis of AD gives the patient time to make choices that maximize quality of life, reduces anxiety about unknown problems, gives more time to plan for the future, and provides a better chance of benefiting from treatment.

There exists a need for highly sensitive and highly specific tests to diagnose Alzheimer's Disease. The present inventors have identified, for the first time, unique Alzheimer's Disease-specific biomarkers useful for the diagnosis of Alzheimer's Disease in a highly sensitive and highly specific manner compared to previously known diagnostic tests. Specifically, the inventors have identified fibroblast growth patterns as biomarkers for the diagnosis of Alzheimer's Disease. Thus, the unique Alzheimer's Disease-specific biomarkers disclosed herein serve as the basis for diagnostic methods having a high degree of sensitivity and specificity for the detection and diagnosis of Alzheimer's Disease. The unique Alzheimer's Disease-specific biomarkers of the present invention may also useful as a model of brain networks and for screening methods to identify compounds which may be used as therapeutic agents in the treatment and prevention of Alzheimer's Disease.

SUMMARY OF THE INVENTION

The instant invention, in certain preferred embodiments, is directed to methods of diagnosing Alzheimer's Disease using assays directed to five separate methodologies, referred to herein as (1) the integrated score methods; (2) the average aggregate area per number of aggregates methods; (3) the cell migration analysis methods; (4) the fractal analysis methods; and (5) the lacunarity analysis methods.

In certain embodiments, the invention is directed to methods of diagnosing Alzheimer's Disease in a human subject comprising the steps of (a) obtaining one or more cells from a human subject; (b) culturing said one or more cells for a time period; (c) determining the average area of cell aggregates and dividing said average area by the number of aggregates to obtain the area per number of aggregates; (d) comparing the determination of step (c) with the area per number of aggregates determined using non-Alzheimer's Disease cells; and (e) diagnosing the presence or absence of Alzheimer's Disease based on the comparison in step (d).

The method is positive for Alzheimer's Disease if the area per number of aggregates determined in step (c) is greater than the area per number of aggregates determined in step (d). In certain preferred embodiments, the difference is statistically significant.

In preferred embodiments, the diagnosis is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In preferred embodiments, the methods disclosed herein use cells that are are fibroblasts although other cells such as blood cells or neural cells may be used.

In certain embodiments, the known non-Alzheimer's Disease cells are AC cells.

In certain embodiments, the cells are cultured in a protein mixture. The protein mixture may comprises an extracellular matrix preparation comprising laminin, collagen, heparin sulfate proteoglycans, entactin/nidogen, and/or combinations thereof. The protein mixture may further comprise growth factor. The extracellular matrix protein may be extracted from a tumor. In certain embodiments, the tumor is the EHS mouse sarcoma.

In certain embodiments, the invention is directed to methods comprising: (a) obtaining one or more cells from a human subject; (b) culturing said one or more cells for a time period; (c) obtaining an image of said cells at the conclusion of said time period; (d) determining a fractal dimension associated with a network of cells on said image; (e) comparing the determination of step (d) with an independently determined fractal dimension associated with known non-Alzheimer's disease cells.

In certain embodiments, if the fractal dimension calculated in step (d) is statistically significantly lower than the fractal dimension associated with known non-Alzheimer's Disease cells, the comparison is indicative of Alzheimer's Disease.

In preferred embodiments, the AD is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In certain embodiments, the fractal dimension is calculated using a box counting procedure. In certain embodiments, the box counting procedure comprises an edge detection procedure.

In certain embodiments, the subject is aged-matched with a control subject providing known non-Alzheimer's disease cells. In certain embodiments, the cell culture period is about 24 hours or about 36 hours or about 48 hours.

In certain embodiments, the cells are cultured in a protein mixture. The protein mixture may comprises an extracellular matrix preparation comprising laminin, collagen, heparin sulfate proteoglycans, entactin/nidogen, and/or combinations thereof. The protein mixture may further comprise growth factor. The extracellular matrix protein may be extracted from a tumor. In certain embodiments, the tumor is the EHS mouse sarcoma.

In certain embodiments, the invention is directed to methods comprising: (a) determining a fractal dimension of an image of a network of fibroblasts from a human subject; (b) determining a fractal dimension of an image of a network of fibroblasts from known non-Alzheimer's disease cells; (c) comparing the determinations of steps (a) and (b).

In certain embodiments, if the fractal dimension determined in step (a) is statistically significantly lower than the fractal dimension determined in step (b), the diagnosis is indicative of Alzheimer's Disease.

In certain embodiments, said subject is aged-matched with a control subject providing said known non-Alzheimer's Disease cells.

In certain embodiments, the invention is directed to methods of diagnosing Alzheimer's disease in a human subject, comprising: (a) calculating a fractal dimension of an image of a network of fibroblasts from said subject; (b) comparing the calculation of step (a) with an independently determined fractal dimension associated with known non-Alzheimer's disease cells; wherein if the fractal dimension calculated in step (a) is statistically significantly lower than the fractal dimension associated with known non-Alzheimer's disease cells, the diagnosis is positive for Alzheimer's Disease in said subject.

In certain embodiments, said subject is aged-matched with a control subject providing said known non-Alzheimer's disease cells.

In certain embodiments, the invention is directed to methods of diagnosing Alzheimer's disease in a human subject, the method comprising: (a) using a surgical blade to obtain a sample of said subject's peripheral skin fibroblasts; (b) using an incubator to incubate said sample for a time period; (c) using an imager to take an image of said sample at the conclusion of said time period; (d) using a computer to calculate a fractal dimension associated with a network of fibroblasts on said image; (e) comparing the calculation of step (d) with an independently determined fractal dimension associated with known non-Alzheimer's disease cells, wherein if the fractal dimension calculated in step (d) is statistically significantly lower than the fractal dimension associated with known non-Alzheimer's disease cells, the diagnosis is positive for Alzheimer's Disease in said subject.

In certain embodiments, the cells are cultured in a protein mixture. The protein mixture may comprises an extracellular matrix preparation comprising laminin, collagen, heparin sulfate proteoglycans, entactin/nidogen, and/or combinations thereof. The protein mixture may further comprise growth factor. The extracellular matrix protein may be extracted from a tumor. In certain embodiments, the tumor is the EHS mouse sarcoma.

In certain embodiments, the invention is directed to methods of diagnosing Alzheimer's Disease in a human subject, the methods comprising: (a) using a surgical blade to obtain a sample of said subject's peripheral skin fibroblasts; (b) using an incubator to incubate said sample for a time period; (c) using an imager to take an image of said sample at the conclusion of said time period; (d) using a computer to calculate a fractal dimension associated with a network of fibroblasts on said image; (e) using a computer to input the fractal dimension of step (d) into a database having fractal dimension data generated from non-Alzheimer's disease cells obtained from control subjects of various ages; (f) using a computer to diagnose said subject by comparing the calculated fractal dimension of step (d) with the data of said database.

In certain embodiments, the sample is incubated in a gelatinous protein mixture.

In certain embodiments, the cells are cultured or incubated in a gelatinous protein mixture. The protein mixture may comprises an extracellular matrix preparation comprising laminin, collagen, heparin sulfate proteoglycans, entactin/nidogen, and/or combinations thereof. The protein mixture may further comprise growth factor. The extracellular matrix protein may be extracted from a tumor. In certain embodiments, the tumor is the EHS mouse sarcoma.

In certain embodiments, the invention is directed to a computer readable medium having a database of fractal dimension data generated from non-Alzheimer's disease cells obtained from control subjects of various ages, said medium containing instructions to: (a) calculate a fractal dimension of an image; (b) compare said fractal dimension with said database of fractal dimension data; and (c) output a diagnosis based on the comparison of step (b).

In certain embodiments, the invention is directed to methods comprising: (a) culturing a skin cell from a human subject for a time period; (b) measuring cell morphology characteristics associated with a network of fibroblasts of said cell; (c) performing a calculation related to said cell morphology characteristics; and (d) comparing the calculation of step (c) with an independently determined parameter associated with known non-Alzheimer's disease cells.

In certain embodiments, the cell morphology characteristics are selected from the group consisting of: number of fibroblast clumps (or aggregates), size of fibroblast clumps (or aggregates), growth of fibroblast clumps (or aggregates), and combinations thereof.

In certain embodiments, the cell morphology characteristics are the presence or absence of big clumps (or aggregates), the presence or absence of cells attached to the clumps (or aggregates), the presence or absence of big clumps (or aggregates) growing, the number of clumps (or aggregates), the presence or absence of remnant edges from a previously formed network of said clumps (or aggregates), the number of cells migrating, the presence or absence of cells being near percolation.

In certain embodiments, the calculation of step (c) comprises assigning a discrete value for each of said cell morphology characteristics and summing said values.

In certain embodiments, the summation is used to diagnose AD or the absence of AD.

In certain embodiments, the cells are cultured in a protein mixture. The protein mixture may comprises an extracellular matrix preparation comprising laminin, collagen, heparin sulfate proteoglycans, entactin/nidogen, and/or combinations thereof. The protein mixture may further comprise growth factor. The extracellular matrix protein may be extracted from a tumor. In certain embodiments, the tumor is the EHS mouse sarcoma.

In certain embodiments, the invention is directed to methods of diagnosing Alzheimer's Disease in a subject comprising the steps of: (a) obtaining one or more cells from said subject and growing said one or more cells in a tissue culture medium; (b) measuring the fractal dimension of said one or more cells over a time period; (c) plotting said fractal dimension as a function of time to obtain a fractal dimension curve; (d) comparing said fractal dimension curve to fractal dimension curves obtained from non-Alzheimer's Disease cells and non-Alzheimer's Disease Dementia (non-ADD) cells; and (e) diagnosing the presence or absence of Alzheimer's Disease in said subject.

In certain embodiments, the diagnosis is positive for Alzheimer's Disease in said subject if said fractal dimension curve measured from a cell or cells obtained from said subject is statistically significantly different from said fractal dimension curves obtained from said non-Alzheimer's Disease cells and said non-ADD cells.

In certain embodiments, said cell or cells obtained from said subject is a fibroblast cell.

In preferred embodiments, the diagnosis is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In certain embodiments, the invention is directed to methods of diagnosing Alzheimer's Disease in a subject comprising the steps of (a) obtaining one or more cells from said subject and growing said one or more cells in a tissue culture medium; (b) determining an integrated score based on one or more characteristics of said cultured cells; (c) comparing said integrated score to an integrated score determined for non-Alzheimer's Disease cells; (d) diagnosing the presence or absence of Alzheimer's Disease in said subject.

In certain embodiments, said characteristics used to calculate said integrated score are selected from the group consisting of aggregate size, attachment of cells to aggregates, evidence of aggregate growth, number of aggregates, edges within networks, evidence of cell migration and closeness to percolation limit (or cell density).

In preferred embodiments, the diagnosis is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In certain embodiments, the invention is directed to methods of diagnosing Alzheimer's Disease in a subject comprising the steps of (a) obtaining one or more cells from said subject and growing said one or more cells in a tissue culture medium; (b) determining the number of migrating cells; (c) comparing the number of migrating cells to the number of migrating cells for non-Alzheimer's Disease cells; (d) diagnosing the presence or absence of Alzheimer's Disease in said subject.

In certain embodiments, the diagnosis is positive for AD if the number of migrating cells obtained from said subject is statistically significantly smaller than the number of migrating non-Alzheimer's Disease cells.

In certain embodiments, said cells are fibroblasts.

In preferred embodiments, the diagnosis is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In certain embodiments, the invention is directed to methods of diagnosing Alzheimer's Disease in a subject comprising the steps of (a) obtaining one or more cells from said subject and growing said one or more cells in a tissue culture medium; (b) determining the lacunarity of said cells; (c) comparing the lacunarity of said cells to the lacunarity of non-Alzheimer's Disease cells; (d) diagnosing the presence or absence of Alzheimer's Disease in said subject.

In certain embodiments, the diagnosis is positive for AD if the lacunarity of the cells taken from said subject is statistically significantly higher than the lacunarity of the non-Alzheimer's Disease cells.

In preferred embodiments, the diagnosis is confirmed using one or more additional diagnostic methods. The method one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

In certain embodiments, said cells are fibroblasts.

In certain embodiments, the invention is directed to methods of screening for a lead compound useful for the development of one or more drug candidates for the treatment or prevention of Alzheimer's disease comprising the steps of (a) growing one or more AD cells in a cell culture medium; (b) contacting said AD cells with a compound; (c) determining whether one or more characteristics of said AD cells is altered to resemble the characteristics of non-Alzheimer's Disease cells that have not been contacted with said compound.

In certain embodiments said cells are fibroblasts.

In certain embodiments, said characteristic is fractal dimension or an integrated score or an average aggregate area per number of aggregates, or cell migration, or lacunarity.

In certain embodiments, the invention is directed to methods of determining Alzheimer's Disease duration in a subject comprising (a) obtaining one or more cells from said subject; (b) measuring cell migration characteristics or average area per number of aggregates for known AD cell lines; (c) preparing standard curves using the data obtained in step (b); measuring migration characteristics or average area per number of aggregates for the cells obtained in step (a) and (d) determining AD disease duration in said subject.

In certain embodiments, said cells are fibroblasts.

In certain embodiments, subjects identified as having AD for 10, 9, 8, 7, 6, 5, 4, 3, 2, or 1 years or less are identified as having increased responsiveness to treatment of AD.

In certain embodiments, the invention is directed to methods of distinguishing between the presence of Alzheimer's Disease (AD) and non-Alzheimer's Disease Dementia (non-ADD) in a subject comprising: (a) obtaining one or more cells from a subject (b) measuring the fractal dimension of said one or more cells over a time period; (c) plotting said fractal dimension as a function of time to obtain a fractal dimension curve; (d) comparing said fractal dimension curve to fractal dimension curves obtained from known non-Alzheimer's Disease cells, known non-Alzheimer's Disease Dementia (non-ADD) cells and known AD cells; and (e) distinguishing between AD and non-ADD in said subject.

In certain embodiments, said cells are fibroblasts.

In certain embodiments, the invention is directed to methods of distinguishing between the presence of Alzheimer's Disease and non-Alzheimer's Disease Dementia in a subject comprising: (a) obtaining one or more cells from a subject (b) obtaining one or more cells from said subject and growing said one or more cells in a tissue culture medium; (c) determining the number of migrating cells; (d) comparing the number of migrating cells to the number of migrating cells for known non-Alzheimer's Disease cells, known AD cells and known non-ADD cells; (e) distinguishing between AD and non-ADD in said subject.

In certain embodiments, said cells are fibroblasts.

In one embodiment, the invention provides a method of diagnosing Alzheimer's disease in a human subject, the method comprising: (a) calculating a fractal dimension of an image of a network of fibroblasts from said subject; (b) comparing the calculations of step (a) with an independently determined fractal dimension associated with known non-Alzheimer's disease cells; wherein if the fractal dimension calculated in step (a) is statistically significantly lower than the fractal dimension associated with known non-Alzheimer's disease cells, the diagnosis is positive, and the diagnosis is negative otherwise; and (c) diagnosing.

BRIEF DESCRIPTION OF THE DRAWINGS

FIG. 11A: Examples of fractal curves and linear fit of the recovery region.
FIG. 11B: Population data showing the slope versus intercept for fractal curves (N=31; $N_{AC}$=10; $N_{AD}$=12; $N_{Non-ADD}$=9).
FIG. 12: Lacunarity analysis.
FIG. 15A: Area per number of aggregates at 48 h and 79 h versus the initial volume of matrigel.
FIG. 15B: Rate of change for area/number as a function of initial volume of matrigel. The graphs illustrate (1) the importance of using 700 µl of Matrigel where the curves show a peak and the effect is maximum. (2) The increase of the Alzheimer's aggregates in size and reduction in number in this time window 40-80 h. This is illustrated in panel A by showing the aggregate area per number at two different time points 48 h and 79 h. The green curve is above the red curve indicating a growth in area and/or reduction in number. Experimentally both are observed. Panel B shows a rate of change in this measure Area/# between 48 h and 79 h. In other words, take the curves from panel A, subtract them and divide by the time interval. The AD fibroblasts cells are unable to migrate away from the aggregates after 40 h. Therefore the aggregates grow bigger for AD cells in this time window. For the control cases, AC, this is not observed and cells are able to migrate away from the aggregates.
FIG. 20A: AD fibroblast cell lines. Graph showing a linear increase of the average aggregate area per number of aggregates with disease duration. In other words, a direct correlation exists between disease duration and the (average aggregate area)/(number of aggregates). The number next to each square is the number of cell lines tested.
FIG. 20B: AD fibroblast cell lines. Linear correlation between disease duration and number of migrating cells. The number next to each square is the number of cell lines tested. Using these correlations, it is possible to identify patients that are in the early, middle or late stages of Alzheimer's Disease. Patients in the earlier stages of the disease have an increased responsiveness to treatment. Knowledge of how long a patient has had Alzheimer's Disease helps guide the therapeutic goals and strategies employed in a treatment regime on a patient-by-patient basis.

DETAILED DESCRIPTION

Figure 1:
FIG. 1: Initial Preparation of Fibroblasts
Figure 1:
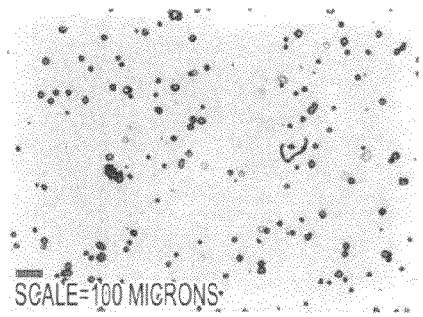
Figure 1:
Figure 1:
Figure 1:
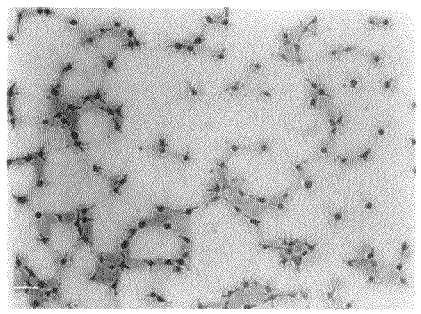
Figure 1:
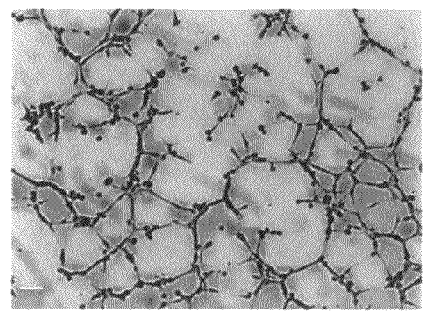
Figure 2:
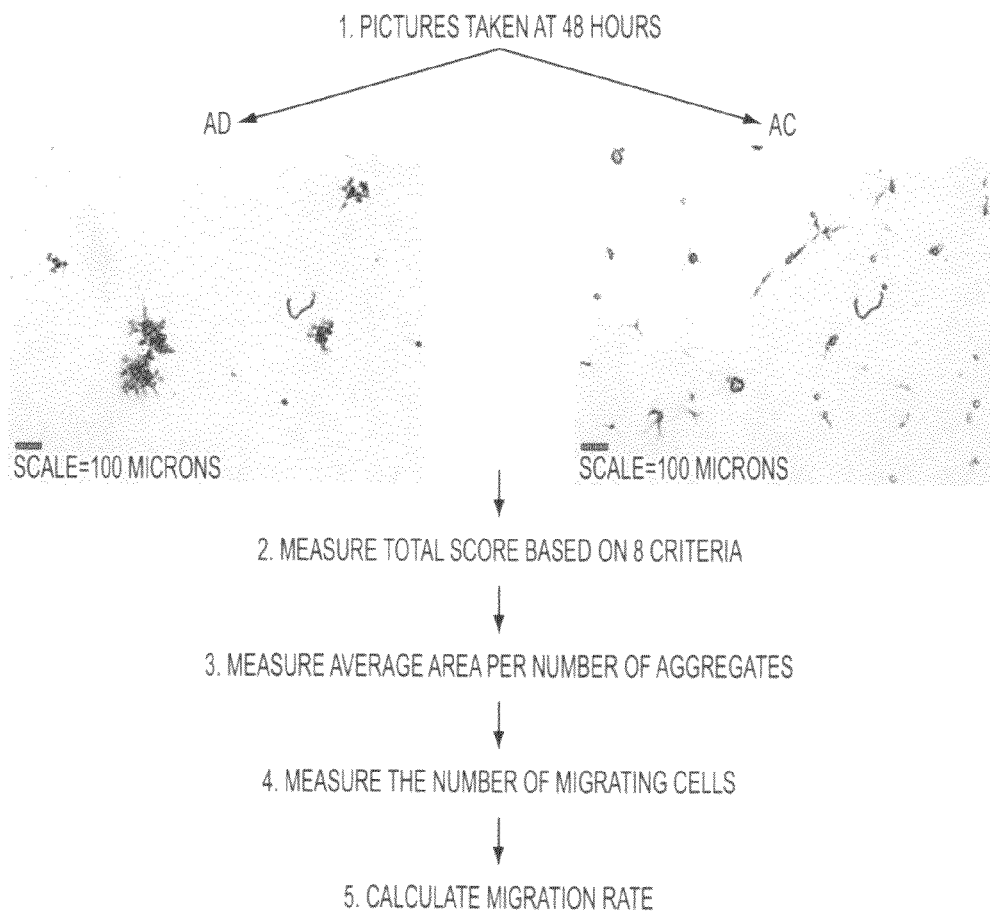
FIG. 2: Integrated Score Protocol

Abbreviations: AC: age matched controls; AD: Alzheimer's Disease; AvC: Average number of cells; DC: density of cells; DMEM: Dulbecco's Modified Eagle Medium; EtOH: Ethanol; FBS: Fetal Bovine Serum; Non-ADD: non Alzheimer's dementias; RM: Room Temperature.

As used herein, "lacunarity" refers to a measure of how a fractal fills space. It is used to further classify fractals and textures which, while they may share the same fractal dimension, appear very visually different. Dense fractals have a low lacunarity. As the coarseness of the fractal increases, so does the lacunarity; intuitively from lacuna meaning "gap" ( . . . more gaps=higher lacunarity). Lacunarity is typically represented by the symbol L.

$$L(r) = \frac{\sum_{m=1}^{r^2} m^2 P(m, r) - \left(\sum_{m=1}^{r^2} mP(m, r)\right)^2}{\left(\sum_{m=1}^{r^2} mP(m, r)\right)^2}$$

The present invention in certain embodiments, is related to methods to diagnose Alzheimer's disease (AD) using peripheral skin fibroblasts. In various embodiments of the invention, quantitative, qualitative, and/or semi-quantitative aspects of the fibroblasts are used to determine the presence or absence of AD.

In one embodiment, the method involves the quantification of the complexity of the human skin fibroblast networks with fractal dimensions measurements. In another embodiment, the method involves calculating a total score based on the sum of characteristics of skin cell fibroblasts. In another embodiment, the method involves calculating the area per number of clumps of skin cell fibroblasts. The methods allow for early screening of AD patients from non-AD dementia, and from age-matched control (AC) cases.

A method to diagnose Alzheimer's disease (AD) using peripheral skin fibroblasts is described. This method quantifies the complexity of human skin fibroblasts patterns of growth with measures of network formation, aggregation, communication, dynamic mobility on a specialized substrate (Matrigel), and fibroblast aggregates morphology.

Matrigel matrix is extracted from mouse sarcoma, rich in extracellular matrix (ECM) proteins. It consists of laminin, followed by collagen IV, heparan sulfate proteoglycans, and entactin 1. At 37° C., matrigel polymerizes to produce biologically active matrix material resembling the mammalian cellular basement membrane. BD Matrigel Matrix Growth Factor Reduced (GFR) is found to be particularly well suited for applications requiring a more highly defined basement membrane preparation of the gel substrate.

Five methods of diagnostic measurements are presented:
1. Method 1: Integrated score
2. Method 2: Average aggregate area per number of aggregates
3. Method 3: Cell migration analysis
4. Method 4 Fractal analysis
5. Method 5: Lacunarity Analysis Additional measures of fibroblasts growth patterns may be developed to diagnostically distinguish between Alzheimer's disease (AD), non Alzheimer's dementia (non-ADD) and age matched controls (AC) cells taken from biopsy. Diagnostic efficacy may be improved by adding extracellular matrix modifying agents.

Method 1—Integrated Score

In this study skin fibroblasts within 1 to 2 hours in culture connect to form measurable networks on matrigel. This condition provides a physiologically relevant environment for studying cell morphology, cellular biochemical functions, cell motility or invasions, and gene expression. After one day these networks degenerate and edges retract to leave behind measurable aggregates.

Eight parameters are used to separate AD fibroblasts from age matched controls (AC) and to non-Alzheimer's dementia (Non-ADD) at 48 hours after plating on matrigel:
1. Existence of large aggregates.
2. Attachment of cells to the aggregates.
3. Evidence of aggregates growing.
4. Small number of aggregates (<10 on a 10× image).
5. Large number of aggregates (>10 on a 10× image).
6. Measurable edges within networks.
7. Evidence of cell migrations.
8. Closeness to percolation limit (cells form continuous streams).

From these 8 parameters a quantitative score is introduced as follows:
1. The first four parameters above are specific to Alzheimer's disease (AD) and score with "−1" for each if present and with "0" if absent.
2. The last four parameters are specific to non-AD and AC, and score with "+1" if present and with "0" if absent.
3. A total score is calculated as the sum of all eight values. If the total score is positive or zero the cells are AC or Non-ADD. If the total score is negative the cells are AD.

Figure 4:
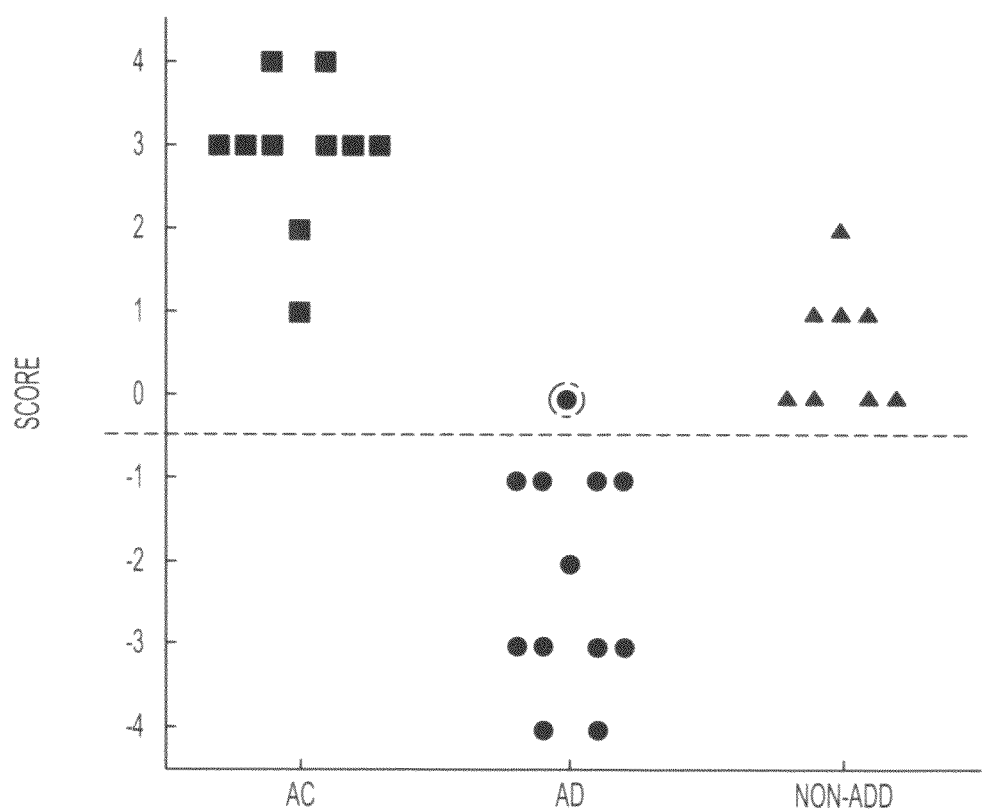
FIG. 4: Integrated Score Method. Total scores representing the sum of eight characteristics for skin cell fibroblasts (AC=age matched controls; AD=Alzheimer's Disease; Non-ADD=Non Alzheimer's such as Parkinson's disease (PD) and Huntington's disease (HD) dementia at 48 hours after plating.

The total score representing the sum of eight characteristics of skin cell fibroblasts at 48 hours after plating is represented in the FIG. 4.

Method 2—Area Per Number of Aggregates

Two of the eight parameters are expressed in the measure area per number of aggregates, which is considerably higher for AD than for AC, and non-ADD (Diagnostic accuracy 96%, N=31 ($n_{AD}$=12, $n_{AC}$=10, and $n_{non-ADD}$=9) p<0.000001 for AD vs AC, and p<0.00001 for AD vs non-ADD).

Figure 5A:
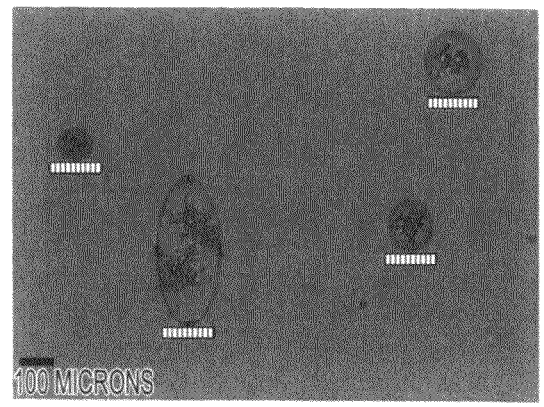
FIGS. 5A and 5B: Examples of aggregates for Alzheimer's disease fibroblasts (A) and normal controls (B). The area was measured in $\mu m^2$ by fitting an ellipse across the aggregates and the aggregates were counted manually on the 10× images. Ellipses were fitted across each aggregate so that the edges of aggregates are inside the ellipse. The same procedure was used uniformly across all the images.
Figure 5B:
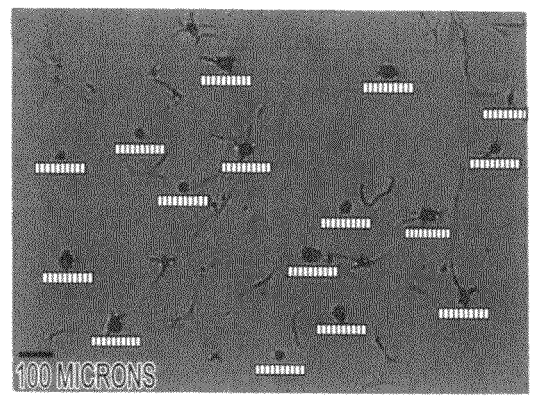

The AD cells show big isolated aggregates, and little or no migrations (FIG. 5A). The normal controls and non-ADD fibroblasts show numerous smaller clumps and high level of migration between the aggregates (FIG. 5B).

Method 3—Cell Migration

Figure 9:
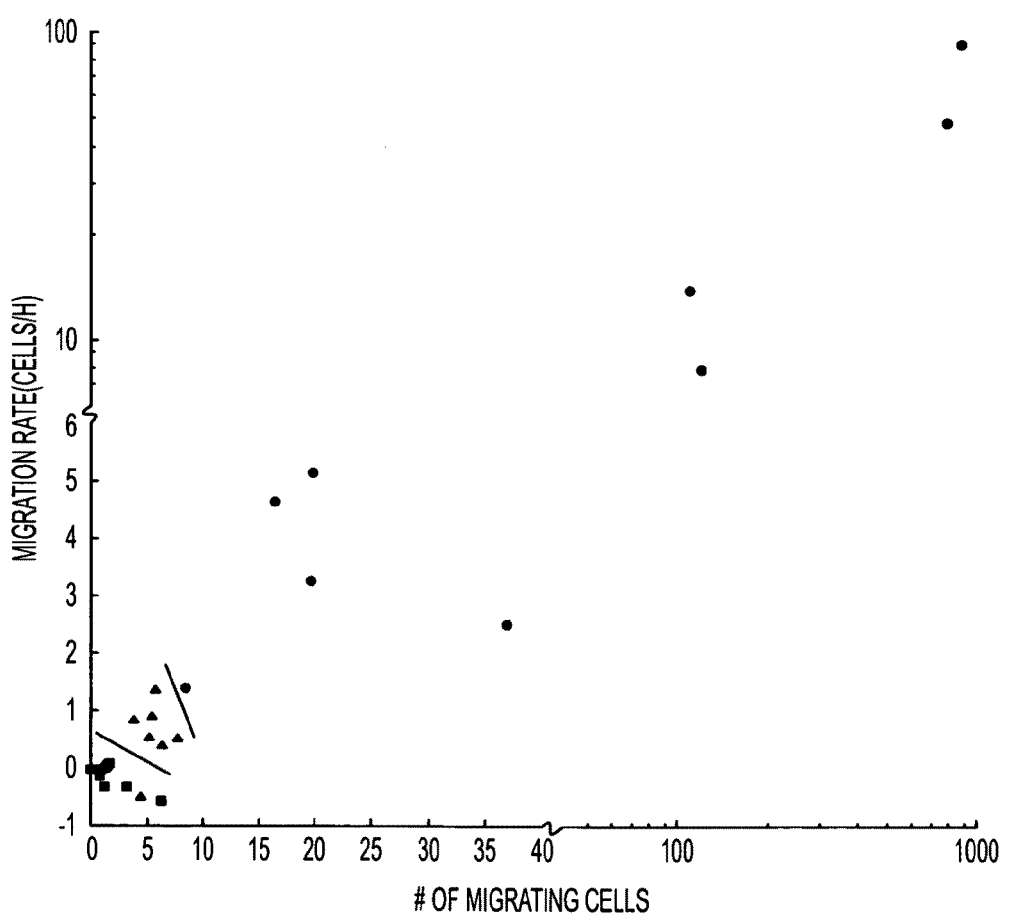
FIG. 9: Migration rate versus number of migrating cells. Green squares-Alzheimer's disease ($n_{AD}$=10), blue triangles-Non Alzheimer's dementia ($n_{Non-ADD}$=7), and red circles-age matched controls ($n_{AC}$=9). Blue lines are separating thresholds.
Figure 10:
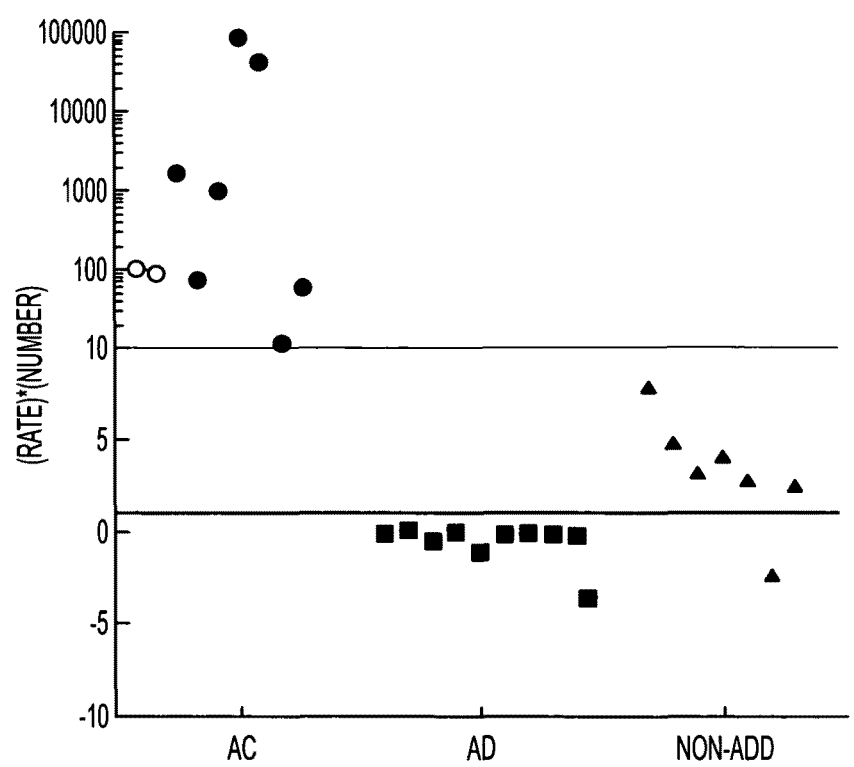
FIG. 10: Migration rate times the number of migrating cells. Green squares-Alzheimer's disease ($n_{AD}$=10), blue triangles-Non Alzheimer's dementia ($n_{Non-ADD}$=7), and red circles-age matched controls ($n_{AC}$=9).

Unlike the Integrated Score Method, the Cell Migration Method is able to distinguish between AD, AC and non-ADD cells. See FIGS. 9 and 10.

Figure 8A:
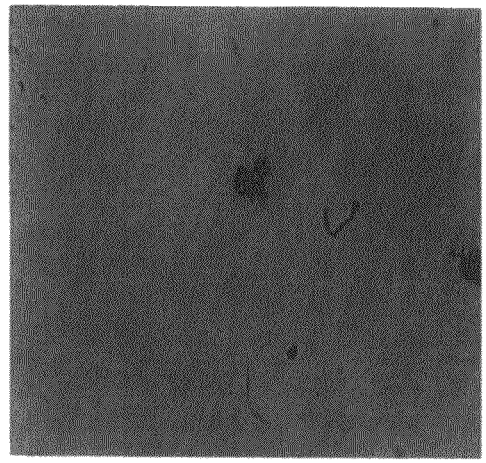
FIGS. 8A and 8B: Examples of freely migrating cells marked with red dots. Left picture (FIG. 8A) Alzheimer's disease (AD) and right picture (FIG. 8B) non Alzheimer's dementia (Non-ADD; Huntington's disease) fibroblasts at 48 hours after plating.
Figure 8B:
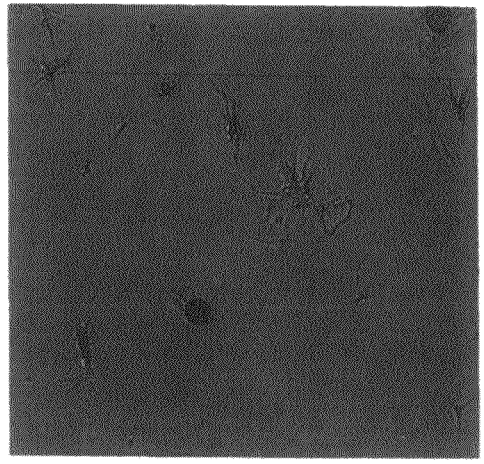

Freely migrating cells are counted at 48 hours, $N_1$, and approximately 7 hours later, $N_2$, and the migration rate is calculated as $R=(N_2-N_1)/\Delta T$, where $\Delta T$ is the time interval between counts. A freely migrating cell is a cell which is not attached to the aggregates, as depicted by the red dots in FIG. 8.

Figure 6:
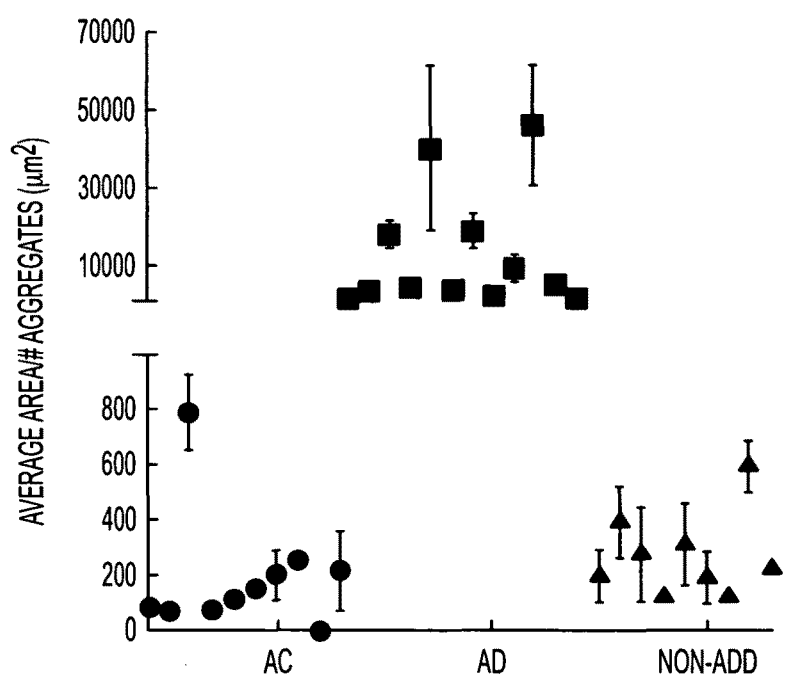
FIG. 6: Fibroblasts at 48 hours. The average area per number of aggregates for 31 cell lines: age matched controls ($N_{AC}$=10), Alzheimer's disease ($N_{AD}$=12), and Non Alzheimer's dementia ($N_{Non-ADD}$=9) such as Parkinson's disease (PD) and Huntington's disease (HD). The error bars represent the standard error of the mean.

The population data (FIGS. 9, 10) shows that Alzheimer's disease fibroblasts (AD-green squares) and non-Alzheimer's dementia fibroblasts (Non-ADD-blue triangles) have a significantly smaller number of migrating cells and rate of migration when compared with age matched control fibroblasts (AC red circles). Alzheimer's disease fibroblasts (green squares) show the smallest number of migrating cells and the lowest migration rate while age matched controls (red circles) show the highest number of migrating cells and the highest migration rate. Interestingly non-ADD cells separate (with one exception) from AD and AC (FIGS. 5 and 6).

From the point of view of migration Non Alzheimer's dementia fibroblasts separate well from Alzheimer's disease fibroblast.

Method 4—Fractal Analysis

Unlike the Integrated Score Method, the Fractal Analysis Method is able to distinguish between AD, AC and non-ADD cells (p<0.01). See FIG. 11B.

Figure 11A:
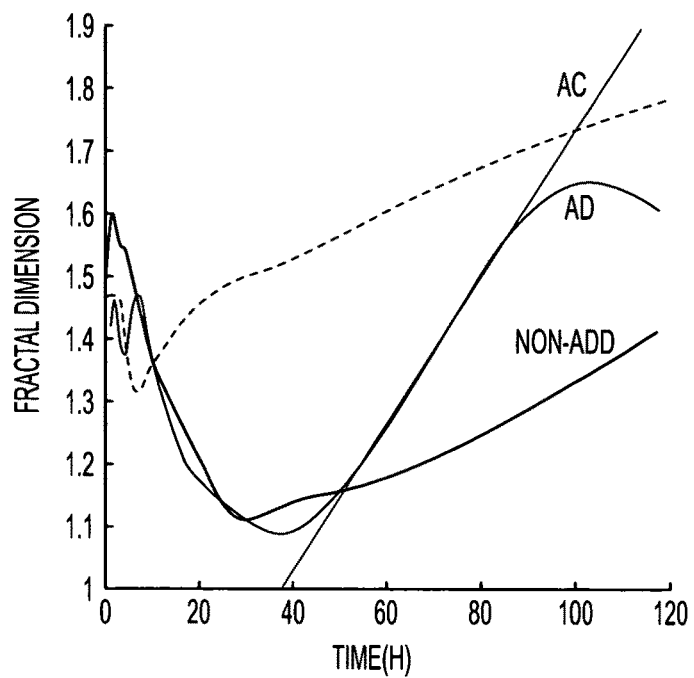
FIGS. 11A and 11B: Fractal analysis.
Figure 11B:
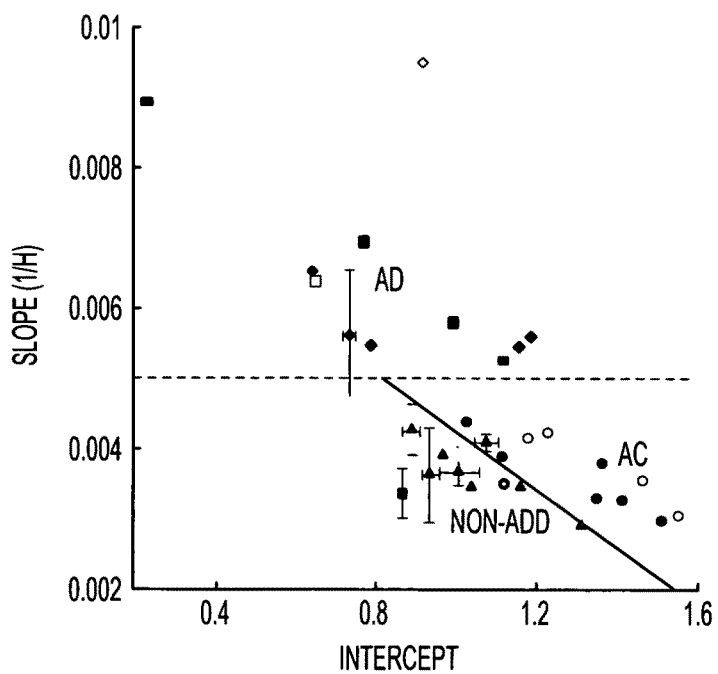

The fractal analysis method utilizes the complexity of the networks as measured by fractal dimension. Cells, preferably fibroblasts, taken from patients suffering from Alzheimer's Disease have a statistically significant lower fractal dimension than AC cells when grown in tissue culture. The complexity of the networks measured by this physical parameter is also markedly different for fibroblasts taken from AD when compared to AC and non-ADD fibroblasts. After network degeneration (~48 h), cells migrate and within a few days reach confluence. This recovery is captured by a linear increase in fractal dimension (FIG. 11A). The slope versus the intercept of each curve that tracks fractal dimension as a function of time is markedly different in the three groups AC, AD and Non-ADD (96% accuracy, n=31 ($N_{AD}$=12, $N_{AC}$=10, $N_{non-ADD}$=9); p<0.0001 for AD vs AC, and p<0.00001 for AD vs non-ADD). Unlike the first method the second one distinguishes between AC and non-ADD (p<0.01) (FIG. 11B).

Method 5—Lacunarity Analysis

Figure 12B:
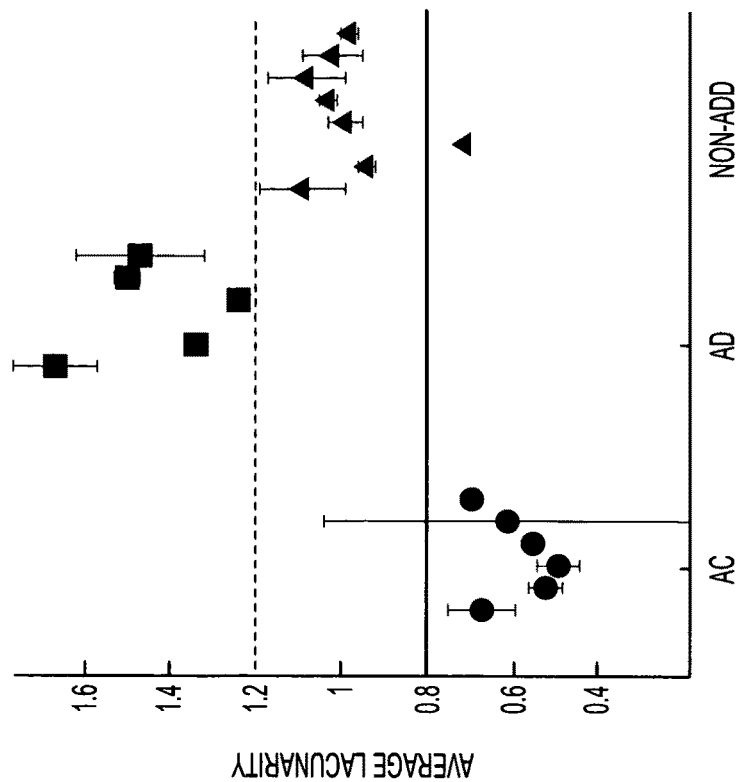
FIG. 12B: Population data showing the average lacunarity (N=8; $N_{AC}$=1; $N_{AD}$=4; $N_{non-ADD}$=3).
Figure 12A:
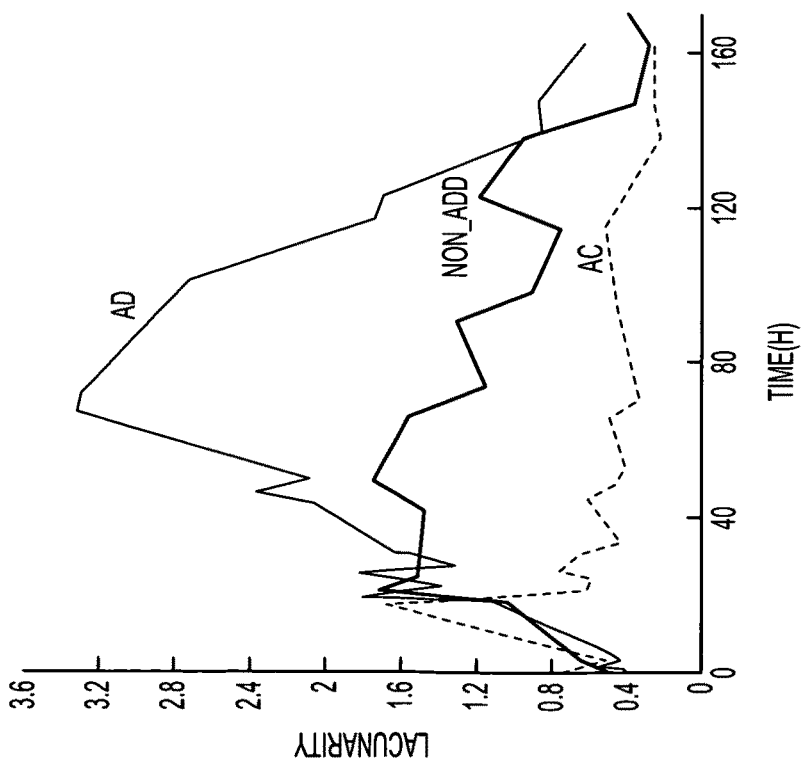
FIG. 12A: Examples of lacunarityl curves.

The lacunarity analysis method quantifies the gaps of the fibroblast patterns and is a complementary measure of complexity used as a second level of discrimination. The average lacunarity of the fibroblasts is also higher for fibroblasts taken from AD when compared to AC and non-ADD fibroblasts. Typically the lacunarity increases and peaks when the network degeneration is maximal i.e. when only isolated aggregates are visible (FIG. 12A). The lacunary drops as the network regeneration starts.

These measures of the dynamics of complexity, offer a new opportunity to diagnose AD patients with a minimally invasive procedure. The simplicity and low cost of the method are a useful screen for AD patients. Human skin fibroblast networks like the neural networks in the AD brain show a reduction in complexity as measured by fractal dimension. Human skin fibroblast networks provide a model of brain networks useful for accurate AD diagnosis and drug screening.

Impaired Vertical Migration of Alzheimer's Disease Fibroblasts.

Figure 13:
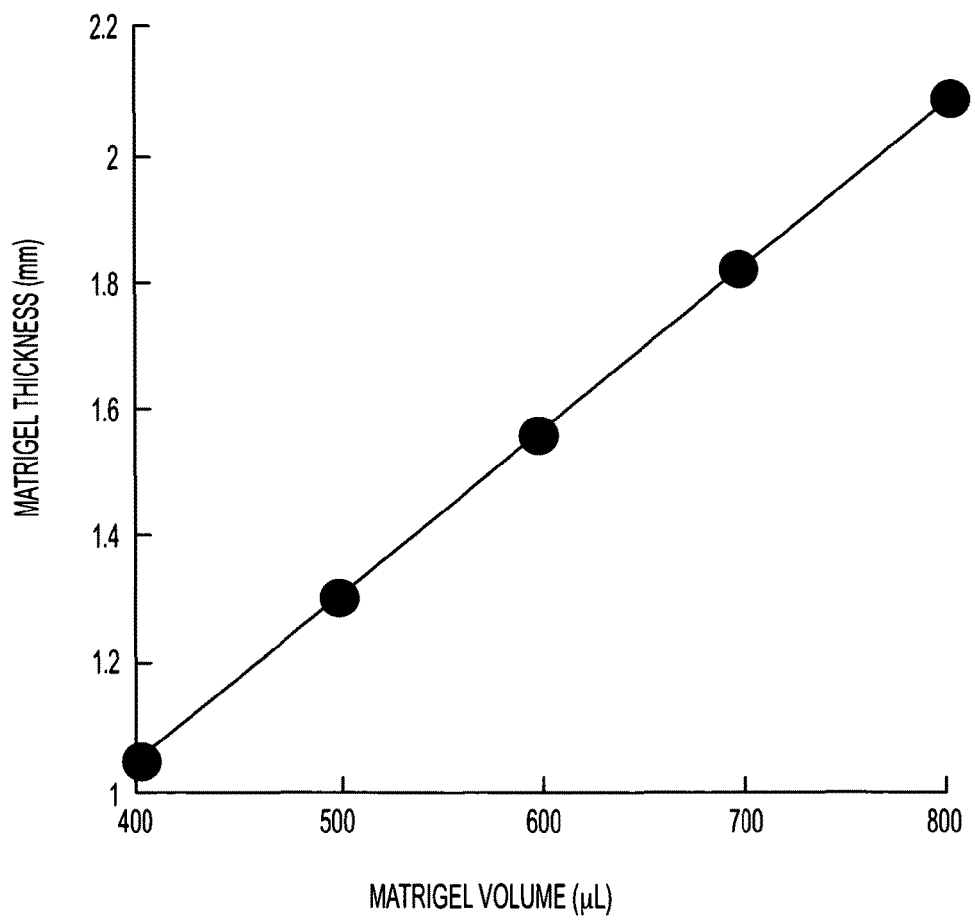
FIG. 13: Proportionality relation between matrigel thickness and volume in 12 well plates. When the matrigel volume is in the range 400 to 800 µl the thickness of the matrigel layer is in the range of 1.04 to 2.08 mm.

The same number of fibroblast cells (50 cells/mm$^3$) was plated on increasing volumes of matrigel, from 400 μl to 800 μl with an increment of 100 μl, on 12 well plates for an AD cell line. The increase in the matrigel volume, V, produces a proportional increase of the thickness of the matrigel layer, h, according to the relation: $V=(\pi r^2)h$, where r=11.05 mm (FIG. 13).

Figure 14A:
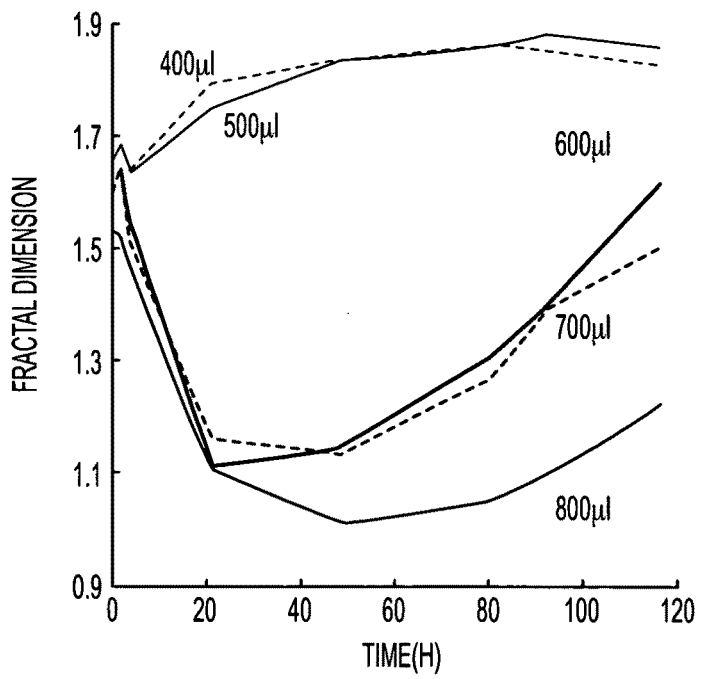
FIG. 14: Sensitivity of fractal dimension, and lacunarity, on the initial volume of matrigel. Fractal dimension (FIG. 14A), and lacunarity (FIG. 14B) have a qualitatively different trend for small volumes of matrigel 400 µl (red) and 500 µl (green) green when compared with larger volumes of matrigel 600 µl (blue), 700 µl (pink), and 800 µl (turquoise). For large volumes (>600 µl) the more matrigel is added the larger the effect on fractal dimension (FIG. 14A), and lacunarity (FIG. 14B). For reference, in all of the previous experiments we used 700 µl of matrigel.
Figure 14B:
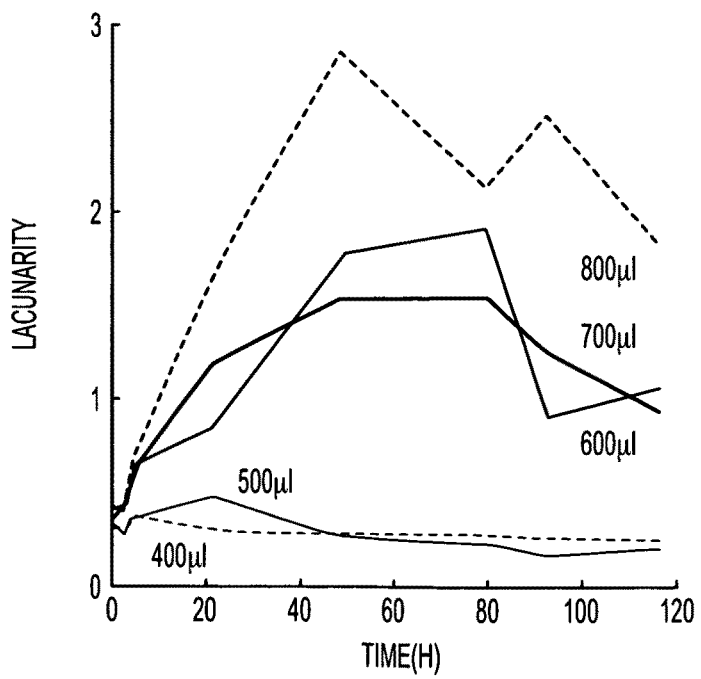

The vertical cell migration from the top surface to the bottom surface becomes more difficult with the increase in the thickness of the matrigel layer. This difficulty in migration is quantified here by the fractal dimension, lacunarity and number (FIG. 14).

Figure 3:
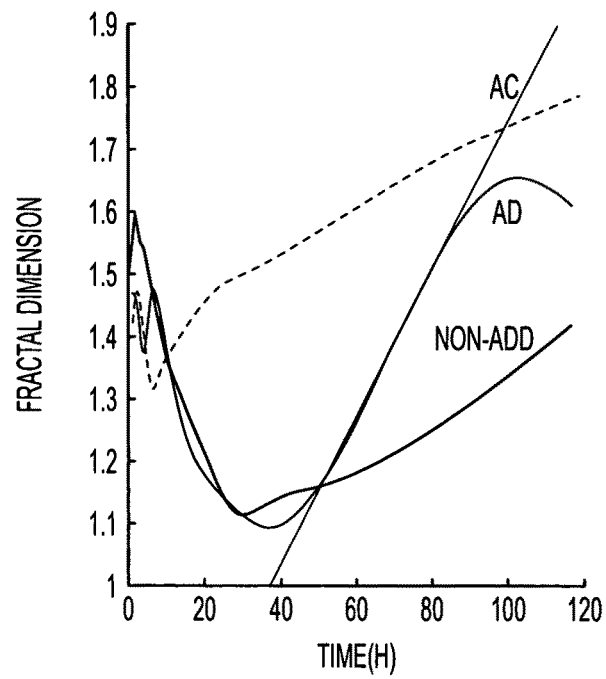
FIG. 3: Fractal Analysis Protocol
Figure 15B:
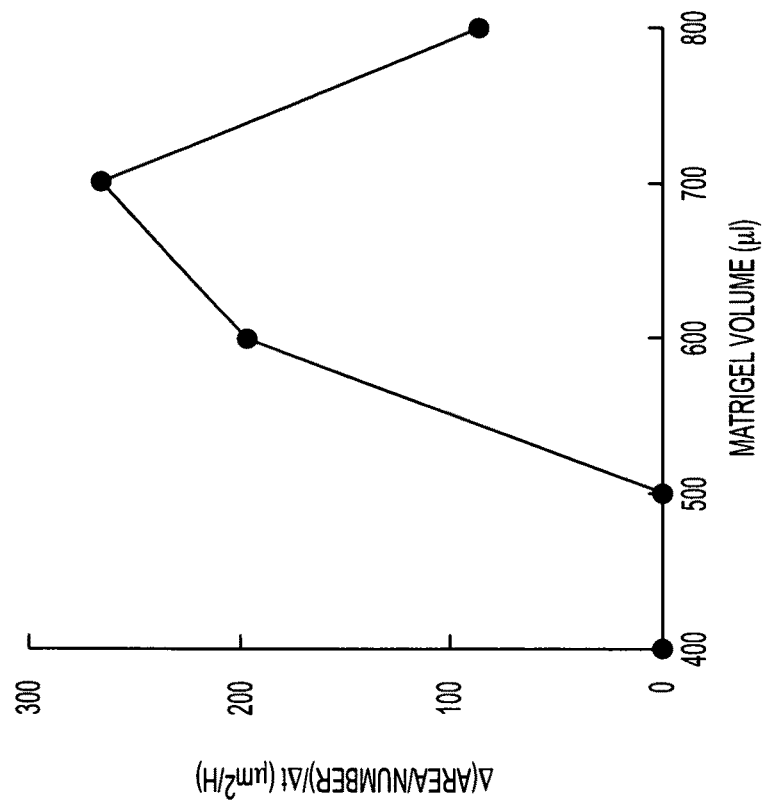
FIGS. 15A and 15B: Sensitivity of AD aggregates at 48 hours on the initial volume of matrigel.
Figure 15A:
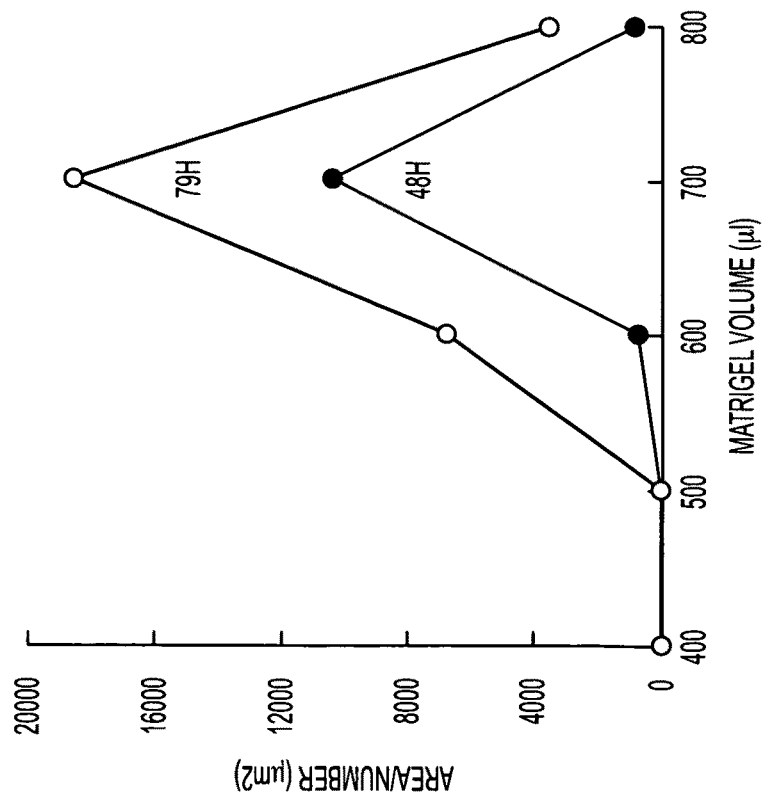

After approximately 24 hours the networks degenerate and aggregates are left behind. Here we show the dependence of the area per number on the initial volume of matrigel (FIG. 12). For small volumes of matrigel, 400, and 500 μl, there are no aggregates while for larger volumes, >500 μl, the area of aggregates divided by their number is a curve which peaks at 700 μl. For a very limited number of the Alzheimer's disease cases the area divided by number of aggregates is near the threshold (see FIG. 6) and a measure of aggregates at a later time will help to better separate these cases. After 79 h these aggregates increase in size and their number decreases so that the ratio area/number increases even further (green curve in FIG. 15A). For both 48 and 79 hours the effect is optimum for an initial volume of 700 μl. The rate of change for the area/number, FIG. 3B, is also a curve with a peak, enforcing the idea that at optimum initial volume of matrigel is 700 μl.

In the experiments presented above we used 1.5 ml Dulbecco's Modified Eagle Medium (DMEM) with 10% fetal bovine serum (FBS) and 1% penicillin/streptomycin (PS). Serum starvation will have a further major perturbation of the measures presented.

Fractal Dimension Methods

In one embodiment, the fractal dimension is calculated using a standard box counting procedure after the raw images, which may be digital images, are filtered through an edge detection procedure which uses, for example the difference of two Gaussians. AD can be diagnosed based on the quantitative image analysis of cultured human skin fibroblasts. In one embodiment, samples are taken through punch-biopsy. In general, a surgical blade can be used. The population data show that AC cases have a significantly higher fractal dimension than that of AD cases. A reduced complexity of human skin fibroblast networks AD cases provides distinctions from AC and non-AD dementia cases.

Other image processing routines can be used with the invention instead of box counting or line detection, The simplicity and low cost of the method is helpful for screening AD patients before resorting to other elaborate and costly techniques. Human skin fibroblast networks, like the neural networks in AD brain, show a reduction in complexity as measured by fractal dimension. In one embodiment, human skin fibroblasts networks may be a model of brain networks that may be useful for new drug screening.

Figure 16:
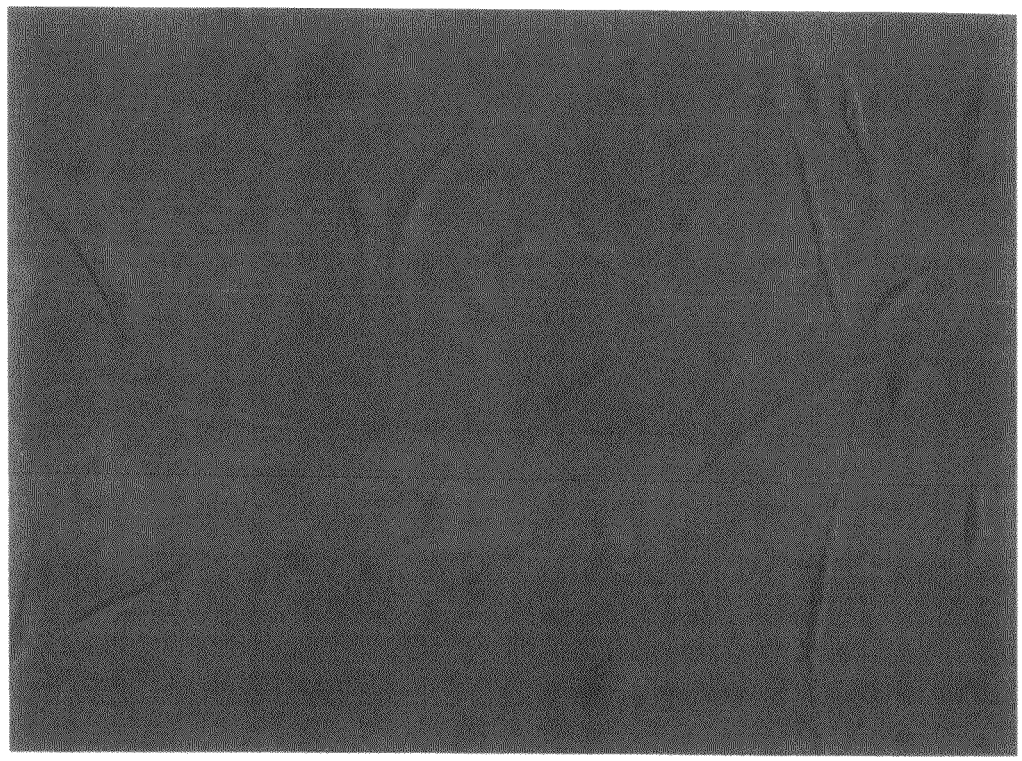
FIG. 16: Depicts age matched control (AC) fibroblasts networks after 24 hours of incubation.
Figure 17:
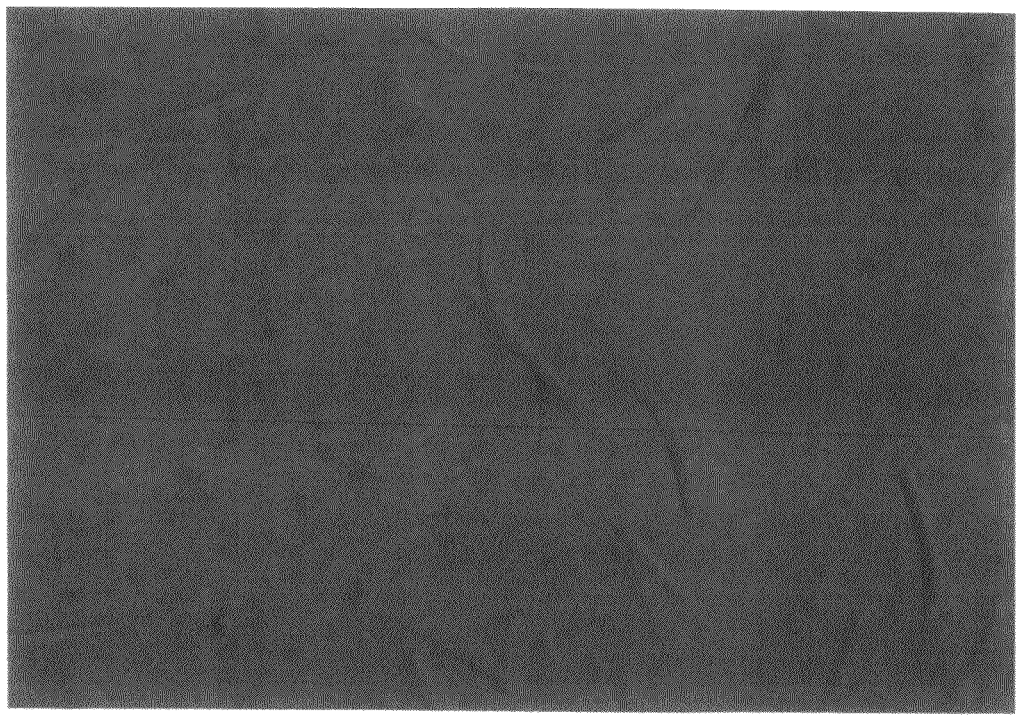
FIG. 17: Depicts Alzheimer's Disease (AD) patient fibroblasts networks after 24 hours of incubation.
Figure 18:
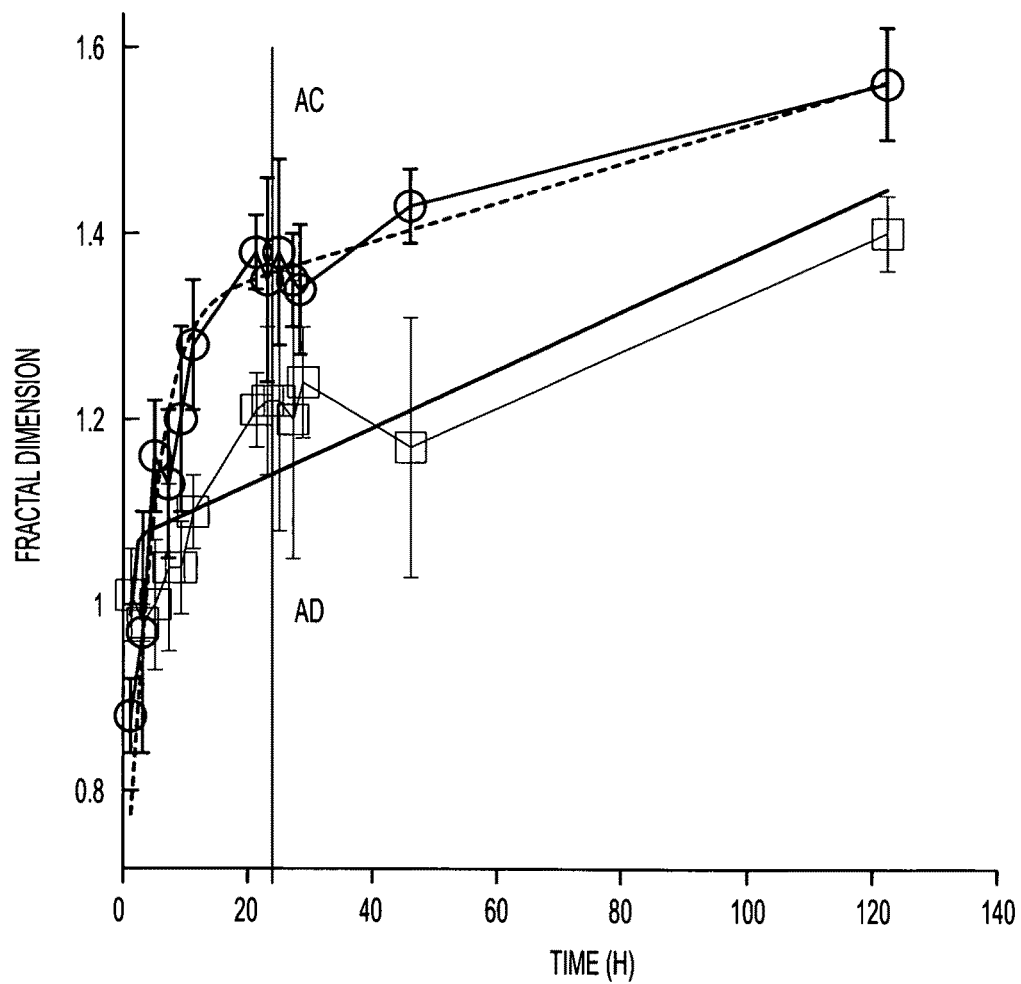
FIG. 18: Depicts the fractal dimensions of AC and AD subjects versus time.
Figure 19:
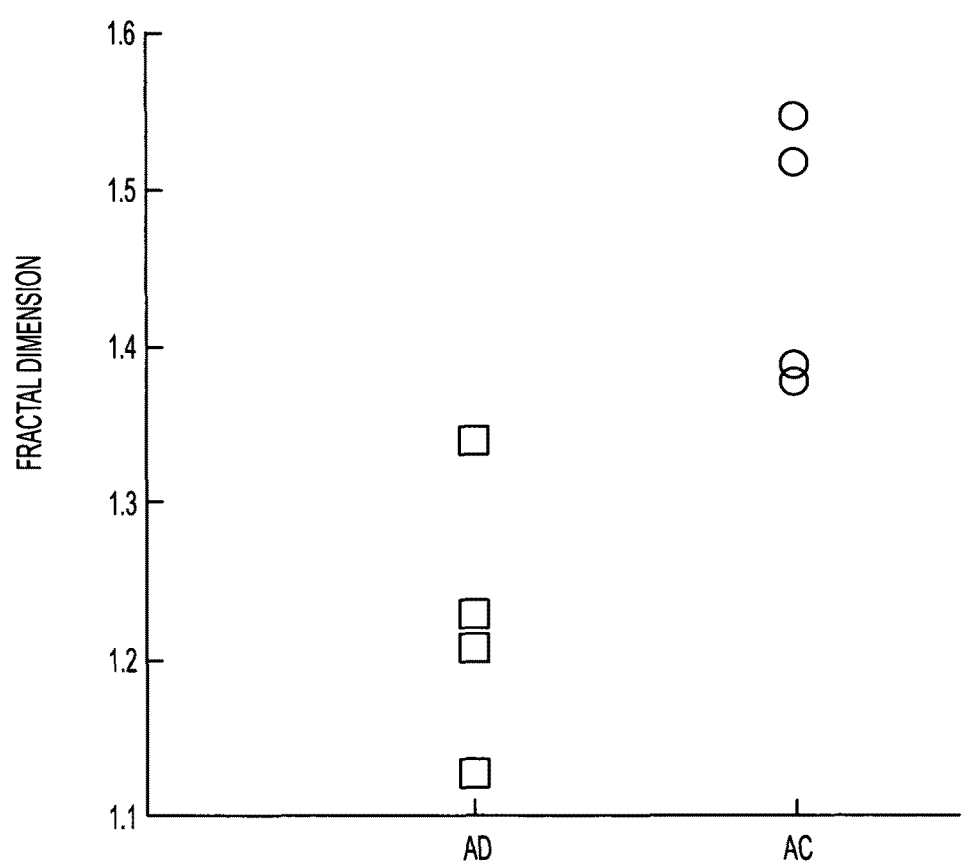
FIG. 19: Depicts the fractal dimension of AD versus AC networks after 24 hours of incubation.
Figure 20B:
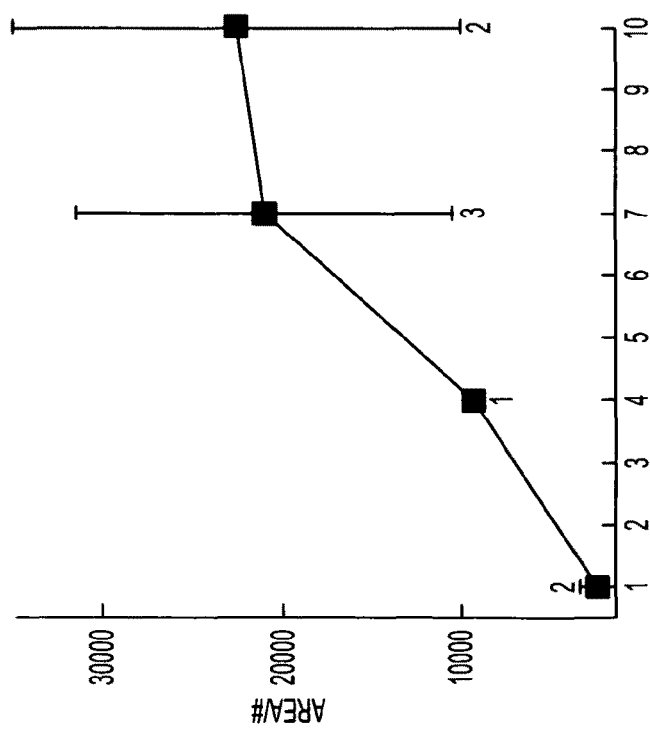
FIGS. 20A and 20B.
Figure 20A:
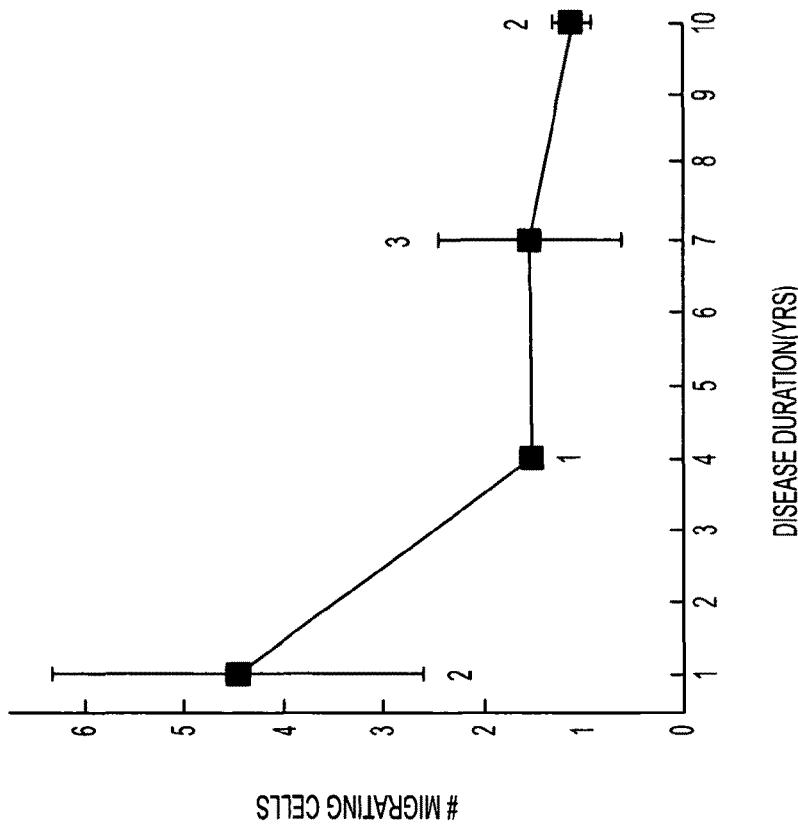

FIG. 16 depicts age matched control (AC) fibroblasts networks after 24 hours of incubation. In one embodiment, a digital image of the network is taken. FIG. 17 depicts Alzheimer's Disease (AD) patient fibroblasts networks after 24 hours of incubation. In one embodiment, a digital image of the network is taken. FIG. 18 depicts the fractal dimensions of AC and AD subjects versus time. The dynamics of cellular network measured by fractal dimension for the two cell lines shows a higher fractal dimension for AC than for AD. A significant separation is noticeable after approximately a few hours of incubation. FIG. 19 depicts a scatter plot the fractal dimension of AD versus AC networks after 24 hours of incubation.

A fractal is generally a rough or fragmented geometric shape that can be split into parts, each of which is (at least approximately) a reduced-size copy of the whole, a property called "self similarity." The object (fractal) need not exhibit exactly the same structure at all scales, but the same "type" of structures must appear on all scales. Human skin fibroblast networks are an example of naturally-occurring fractals.

Consider a line. If the line is subdivided in half, it takes two of these halves to recreate the original line. If the line is subdivided into four pieces, it takes four of them to cover the line. Generally, given a line segment of length "s," the number of segments that will cover the original line is given by $N(s)=(1/s)^1$.

Consider a square. If the square is subdivided into smaller squares, each with one half the side length then it takes four ($2^2$=4) of these smaller squares to form the original square. If the square is subdivided into smaller squares each with one quarter of the side length then it takes sixteen ($2^4$=16) of them to form the original square. As above we can write an expression for the number of pieces we need of size "s" to cover the original square, it is $N(s)=(1/s)^2$. For a cube, the result is $N(s)=(1/s)^3$.

The exponents 1, 2, and 3 in the above examples are the dimensions of the line, square, and cube respectively. This can be generalized to $N(s)=(1/s)^D$ here D is the dimension, an integer as above, but it need not be. If we take logarithms of both sides we have $\log(N(s))=D\log(1/s)$, in order words we can estimate the dimension by plotting $\log(N(s))$ against log (1/s) the slope (D) of which is the dimension. If the slope is a non-integer, than the object is a fractal, and the dimension is a fractional (fractal) dimension.

Complexity is the study of how living and nonliving things organize themselves into patterns and interact as systems. Complexity is extremely multidisciplinary and involves scientists in a vast assortment of fields from biology to physics. Complexity of human skin fibroblast networks can be quantified by computing their fractal dimensions.

In one embodiment, edge detection is used in the present invention. Edge detection is a term used in the field of image processing, particularly in the areas of feature detection and feature extraction, to refer to algorithms which aim at identifying points in a digital image at which, for example, the image brightness changes sharply or has other discontinuities.

It can be shown that under rather general assumptions for an image formation model, discontinuities in image brightness are likely to correspond to one or more of discontinuities in depth, discontinuities in surface orientation, changes in material properties and variations in scene illumination.

In the ideal case, the result of applying an edge detector to an image may lead to a set of connected curves that indicate the boundaries of objects, the boundaries of surface markings as well curves that correspond to discontinuities in surface orientation. Thus, applying an edge detector to an image may significantly reduce the amount of data to be processed and may therefore filter out information that may be regarded as less relevant, while preserving the important structural properties of an image. If the edge detection step is successful, the subsequent task of interpreting the information content in the original image may therefore be substantially simplified.

There are many methods for edge detection, but most of them can be grouped into two categories, search-based and zero-crossing based. The search-based methods detect edges by first computing a measure of edge strength, usually a first-order derivative expression such as the gradient magnitude, and then searching for local directional maxima of the gradient magnitude using a computed estimate of the local orientation of the edge, usually the gradient direction. The zero-crossing based methods search for zero crossings in a second-order derivative expression computed from the image in order to find edges, usually the zero-crossings of the Laplacian or the zero-crossings of a nonlinear differential expression. As a pre-processing step to edge detection, a smoothing stage, for example Gaussian smoothing, may be applied. In other embodiments noise filtering algorithms may be employed.

The edge detection methods that have been published mainly differ in the types of smoothing filters that are applied and the way the measures of edge strength are computed. As many edge detection methods rely on the computation of image gradients, they also differ in the types of filters used for computing gradient estimates in the x- and y-directions.

In one embodiment, the method uses a box counting procedure. The image is covered with boxes, for example by a computer. The goal is to find how the number of boxes needed to cover the image changes with the size of the boxes. If the object is 1-dimensional, such as a line, we expect $N(s)=(1/s)^1$, as described above. And so on for higher dimensions. Such a procedure can be implemented on a computer using the digital images of the samples.

In one embodiment a database can be made of many different non-Alzheimer's control (AC) subjects of various ages. The database can be made such that the human subject being tested can be evaluated versus age-matched AC data.

In one embodiment, the complexity of the fibroblast networks is quantified by measurement of fractal dimension and lacunarity curves. The complexity of the networks measured by these physical parameters also markedly differs for fibroblasts taken from AD when compared to AC and non-ADD fibroblasts. After network degeneration, by way of example after approximately 48 hours, cells migrate and within a few days reach confluence. In one embodiment, this recovery is captured by a linear increase in fractal dimension. The slope versus the intercept of each curve that tracks fractal dimension as a function of time is markedly different in the three groups AC, AD, and non-ADD (100% accuracy, n=26 (AD=10, AC 10, non-ADD=6); p<0.0001 for AD vs AC, and p<0.00001 for AD vs non-ADD). This method shows distinguishable differences between AC and non-ADD (p<0.01).

Methods Utilizing Cell Morphology Characteristics

Within a short time after being cultured, for example within an hour, measurable networks form. In one embodiment, culturing takes place in a gelatinous protein mixture which provides a viable environment for studying cell morphology. After a time, for example after about one day, these networks degenerate and edges retract to leave behind measurable "clumps" or aggregates.

As with any of the methods of the invention, the image may be prepared by obtaining a cell or a sample and culturing or incubating the cell or sample for a period of time. In one embodiment, the period of time is about 48 hours or any one hour increment subdivision thereof. During the period of time, the cell or sample fibroblast network changes. An image is then taken. Quantitative, qualitative, and semi-quantitative information can be gathered from the image.

In one embodiment, certain characteristics of the image can be assigned values. For example, by inspecting the image, the following non-exhaustive, and non-limiting characteristics can be ascertained and optionally assigned values: (1) Are there big clumps? (2) Are the cells attached to the clumps? (3) Are the big clumps growing? (4) Are there just a few clumps? For example, less than or equal to five on a 10× image? (5) Are there multiple clumps (for example, greater than five on a 10× image)? (6) Are there remnant edges from a network previously formed (for example, in matrigel)? (7) Are there many cells migrating? (8) Are the cells near percolation (i.e., cells which form a substantially continuous stream from left right or up down of the image)?

In some embodiments, only a partial listing of these characteristics may be considered. Two of the eight parameters are expressed in the ratio of a measured area per number of aggregates. This ratio is considerably higher for AD than for age matched controls (AC), and non-Alzheimer's degeneration (non-ADD) (Diagnostic accuracy 96%, N=30 (AD=12, AC=10, and non-ADD=8) p<0.000001 for AD vs AC, and p<0.00001 for AD vs non-ADD). Any or even all of these characteristics can be ascertained manually or via image processing methods as is known in the relevant arts.

In one embodiment, the "characteristics," for example the eight characteristics (or a subset thereof or an augmented set of characteristics) are assigned values. The values can be assigned according to correlation studies, for example according to being correlated with AD cells or being correlated with AC or non-ADD cells. In one embodiment, the characteristics (1) through (4) mentioned above are correlated with AD fibroblasts, and are then assigned a value of, for example −1 if present or 0 if absent. The actual values are given by way of example only, as other values can also be assigned. In one embodiment, characteristics (5) through (8) mentioned above are correlated with AC and non-ADD fibroblasts. Parkinson's Disease (PD) and Huntington's Disease (HD) are non-limiting examples of non-ADD cells. Characteristics (5) through (8) are assigned a value of +1 if present or 0 if absent. In one embodiment, the assigned values can be summed for each clump. The summed values can then be plotted, as is shown in FIG. 4.

In another embodiment, the values of the characteristics can be assigned intermediate values according to the "strength" of the characteristic being measured. For example, the characteristic (1) "are there big clumps"? can be assigned any intermediate value between −1 (for extremely large clumps) through zero (for extremely small clumps). For example, a value of −0.9 can be assigned for relatively "large" clumps, a value of −0.8 assigned to slightly smaller (yet still "large") clumps, and so on. A graduated scale for any of the above-mentioned characteristics (or others) can be formulated through routine experimentation. In one embodiment, the method can be fully automated using image processing techniques, and moreover all (or perhaps only some) of the characteristics can be quantified on a fully graduated, i.e., digital, basis.

As illustrated in FIG. 4, AD cells, such as those shown in FIG. 5A characteristically display big isolated clumps with little to no migration compared to AC cells and non-ADD cells. Consequently, the AD cells typically have values summing to relatively low numbers, typically negative numbers, in this scheme. The normal controls and non-ADD fibroblasts, such as those shown in FIG. 5B show numerous smaller clumps and high level of migration between the clumps. Consequently, the AC and non-ADD cells typically have values summing to relatively high numbers, typically positive numbers, in this scheme. The above method provides yet another way for diagnosing AD.

Methods Utilizing Area

In another embodiment, the area of clumps is calculated. For example, the area of the clumps shown in FIG. 5B (AC cells) is calculated. This can be done by any suitable method, for example but not limited to, by fitting an ellipse across the clump. The clumps can then be counted on the images. The counting as well as area calculation can either be done manually or can be automated, for example by image processing techniques known in the relevant arts. The numbers shown on FIG. 5B represent the area of the clumps in square microns, $\mu^2$. Similarly, the area of AD cells, such as those shown in FIG. 5A, can be calculated. By way of example, the area shown on FIG. 5A is $12,670\mu^2$, a much larger area than associated with the areas of the AC cells depicted in FIG. 5B. The area per number of clumps can be plotted as is depicted in FIG. 7.

Figure 7:
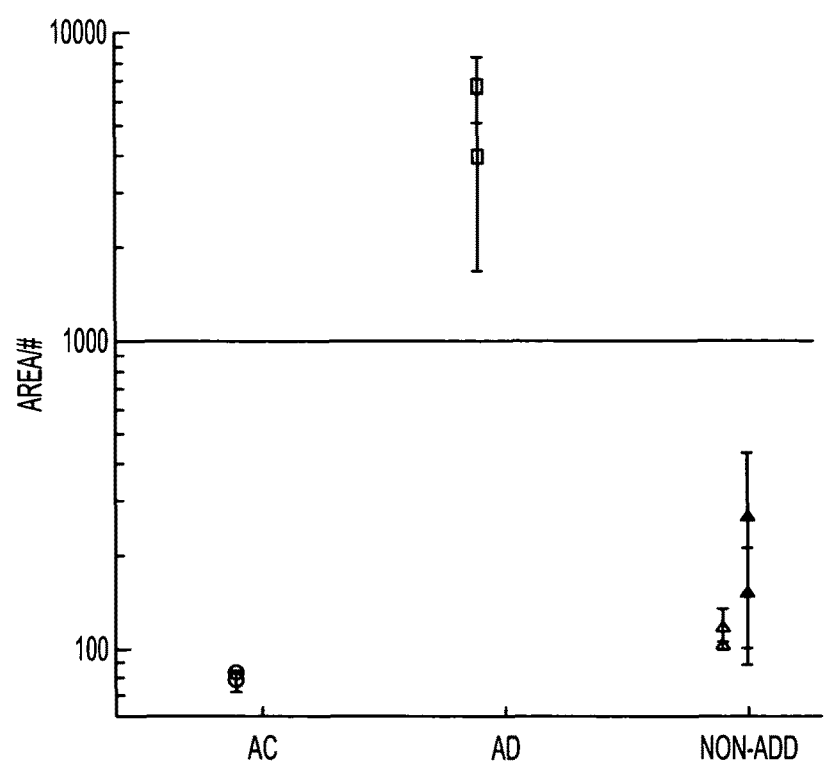
FIG. 7: Repeatability of the results. The average area per number of aggregates for four repeated cell lines. Experiments were at least one month apart for the same cell lines. Initial number of cells was within 10%.

FIG. 7 is a logarithmic plot of the area per number of clumps as calculated by the above method. Of note, the area per number of clumps for AD cells is significantly higher than the area per number of clumps for either the AC or the non-ADD cells. The above method provides yet another way for diagnosing AD.

In other embodiments of the invention, any of the above methods can be combined. For example, the fractal dimension can be calculated, and/or the characteristics can be assigned and summed, and/or the area per number of clumps can be calculated. In one embodiment, a positive diagnosis for AD is made only when two or more of the above methods independently would indicate a positive diagnosis. In other embodiments, a positive diagnosis for AD is made only when all methods (for example three different methods, specifically for example, the fractal dimension, summation of characteristics, and area methods) would independently indicate a positive diagnosis. In other embodiments, false positives and negatives can be avoided or minimized by adjusting the definition of "statistically significant," for example by setting a diagnosis threshold at a certain multiple of population standard deviations for any of the above mentioned variables.

In any embodiments of the invention, a cell may be cultured or incubated in a protein mixture. In one embodiment, the protein mixture is a gelatinous protein mixture. A non-limiting exemplary gelatinous protein mixture is Matrigel™. Matrigel™ is the trade name for a gelatinous protein mixture secreted by Engelbreth-Holm-Swarm (EHS) mouse sarcoma cells and marketed by BD Biosciences. This mixture resembles the complex extracellular environment found in many tissues and is used by cell biologists as a substrate for cell culture. BD Bioscience maintains a website at http://www.bdbiosciences.ca.

In one embodiment, a cell is cultured or incubated in a basement membrane preparation. In one embodiment, this preparation is solubilized. In one embodiment, a basement membrane preparation is extracted from a tumor. In one embodiment, the tumor is the Engelbreth-Holm-Swarm (EHS) mouse sarcoma, a tumor rich in extracellular matrix proteins. Its major component is laminin, followed by collagen IV, heparan sulfate proteoglycans, entactin/nidogen. In certain embodiments, this preparation contains TGF-beta, epidermal growth factor, insulin-like growth factor, fibroblast growth factor, tissue plasminogen activator, and/or other growth factors which may or may not occur naturally in the EHS tumor.

In one embodiment, a cell is cultured or incubated in a preparation comprising extracellular matrix proteins. In one embodiment, the preparation comprises laminin, collagen, heparin sulfate proteoglycans, entactin/nidogen, and/or combinations thereof. In one embodiment, the preparation is extracted from a tumor. In one embodiment, the tumor is the Engelbreth-Holm-Swarm (EHS) mouse sarcoma. In one embodiment, the preparation further comprises growth factor. In one embodiment, the preparation further comprises TGF-beta, epidermal growth factor, insulin-like growth factor, fibroblast growth factor, tissue plasminogen activator, and/or combinations thereof, and/or other growth factors. In one embodiment, the TGF-beta, epidermal growth factor, insulin-like growth factor, fibroblast growth factor, tissue plasminogen activator, and/or other growth factors occur naturally in a tumor. In one embodiment, the growth factors occur naturally in the EHS mouse sarcoma.

In one embodiment, the preparation comprises an extracellular matrix protein preparation which is effective for the attachment and differentiation of both normal and transformed anchorage dependent epithelioid and other cell types. These include neurons, hepatocytes, Sertoli cells, chick lens, and vascular endothelial cells. In one embodiment, the extracellular matrix protein preparation may influence gene expression in adult rat hepatocytes as well as three dimensional culture in mouse and human mammary epithelial cells. In one embodiment, this is the basis for several types of tumor cell invasion assays, will support in vivo peripheral nerve regeneration, and provides the substrate necessary for the study of angiogenesis both in vitro and in vivo. In one embodiment, an extracellular matrix protein also supports in vivo propagation of human tumors in immunosuppressed mice.

In one embodiment, a volume of chilled extracellular matrix protein is dispensed onto tissue culture labware. As used herein, "chilled" refers to a temperature less than room temperature, preferably less than about 15° C., more preferably less than about 10° C., more preferably less than about 5° C., most preferably about 4° C. When incubated at an elevated temperature, the extracellular matrix proteins self-assemble producing a thin film that covers the surface of the labware. As used herein, "elevated" refers to a temperature above room temperature, preferably above about 20° C., more preferably above about 25° C., more preferably above about 30° C., more preferably above about 35° C., and most preferably about 37° C., which is approximately average human body temperature.

Cells cultured on extracellular matrix protein demonstrate complex cellular behavior that is otherwise difficult to observe under laboratory conditions. For example, endothelial cells create intricate spiderweb-like networks on extracellular matrix protein coated surfaces but not on plastic surfaces. Such networks are highly suggestive of the microvascular capillary systems that suffuse living tissues with blood. Hence, the process by which endothelial cells construct such networks is of great interest to biological researchers and extracellular matrix proteins allow them to observe this.

In some embodiments, it may be preferable to use greater volumes of extracellular matrix proteins to produce thick three-dimensional gels. The utility of thick gels is that they induce cells to migrate from the surface to the interior of the gel. In some embodiments, this migratory behavior is studied by researchers as a model of tumor cell metastasis.

The ability of extracellular matrix proteins to stimulate complex cell behavior is a consequence of their heterogeneous composition. In some embodiments, the chief components of extracellular matrix proteins are structural proteins such as laminin and collagen which present cultured cells with the adhesive peptide sequences that they would encounter in their natural environment. Some embodiments also employ growth factors that promote differentiation and proliferation of many cell types. Extracellular matrix proteins may also contain numerous other proteins in small amounts.

Measures of the dynamics of fibroblast network complexity, as disclosed herein, offer a new opportunity to diagnose AD patients with a minimally invasive procedure. Human skin fibroblast networks, like the neural networks in the AD brain, show a reduction in complexity as measured by fractal dimension compared to AC and non-ADD cells. Human skin fibroblast networks provide a model of brain networks useful for accurate AD diagnosis and drug screening.

All books, articles, or patents references herein are incorporated by reference to the extent not inconsistent with the present disclosure. The present invention will now be described by way of examples, which are meant to illustrate, but not limit, the scope of the invention.

EXAMPLE 1

Coating the 12 Well Plates with BD Matrigel Matrix Growth Factor Reduced

Equipment and Materials: Class II A/B 3 biological safety cabinet (Form a Scientific). $CO_2$ water jacket incubator (Form a Scientific). Inverted microscope. Pasteur pipettes. Serological pipettes. Pipette aids (Omega Cat. No. P5017). BD Matrigel Matrix Growth Factor Reduced (BD Biosciences, Cat. No, 354230), (Aliquot 800 µl and store at −20° C.). Sterile 12 well culture plates (Corning Inc., Cat. No. 3512)

Procedure: Thaw BD Matrigel Matrix Growth Factor Reduced at 4° C. on ice 30 min. before use, and use pre-cooled pipettes, tips, and 12 well culture plates. Make sure Matrigel is liquid and has no solid aggregates.

Thick Gel Method: Using cooled pipettes, mix the BD Matrigel Matrix Growth Factor Reduced to homogeneity. Keep 12 well culture plates on ice 30 min. prior to use and during the adding of BD Matrigel Matrix Growth Factor Reduced, 700 µL per well. Verify the homogeneity of the gel on the surface of the cell culture plates under the inverted microscope, and avoid bubbles. Place 12 well plates at 37° C. for 30 minutes. Add the cell suspension on top of BD Matrigel Matrix Growth Factor Reduced. The density of cells is adjusted to 50 cells/mm$^3$ (See below).

EXAMPLE 2

Preparing of Human Skin Fibroblast for Plating

Equipment and Materials: Class II A/B 3 biological safety cabinet (Form a Scientific). $CO_2$ water-jacket incubator (Form a Scientific). Inverted microscope. T-E (Trypsin-EDTA solution 1×) (stored at −20 C). M-2 (Medium-2) DMEM with 10% FBS, and 1% PS. Pasteur pipettes. Serological pipettes. Pipette aids (Omega Cat. No. P5017). Culture flask, vent cap, 25 cm$^2$. 15 ml and 50 ml sterile plastic tube. 500 ml Bottle Top Filter. Water bath Centrifuge.

Procedure: Thaw and warm T-E and M-2 medium at 37° C. in the water bath.

Flask cultures containing tissue fragments: Remove and discard culture medium from flask by suction. To eliminate serum residue that could inactivate trypsin, add 2 ml T-E and suck out immediately. Add 2 ml of T-E to flask and incubate at 37° C. for 3-5 minutes. Time of detachment of cells from the surface of culture flasks is not the same for all patients and needs to be adjusted for each case in the range 3-5 minutes. Observe the cells under microscope: if rounded, they are detached. If most are not rounded, leave the suspension in the incubator for another minute or two until they appear rounded. Add 5 ml of M-2 medium to inhibit trypsin activity. Gently triturate by pipetting to detach cells from the bottom of the flask, but be careful not to touch, or detach, the tissue fragments. Transfer the cells suspension (by pipette) to a 15 ml sterile plastic tube, centrifuge it at 1000 RPM (speed 3) for 5 minutes, discard the supernatant, and suspend the cells in 3 ml M-2 medium. Gently triturate by pipetting to detach cells from the bottom of the 15 ml sterile plastic tube.

EXAMPLE 3

Counting of Human Skin Fibroblasts

Equipment and Materials: Class II A/B 3 biological safety cabinet (Fauna Scientific). Inverted microscope. Cell counting chamber-Levy Double (VWR scientific, Cat. No. 15170-208). Pasteur pipettes. Serological pipettes. Pipette aids (Omega Cat. No. P5017). Sterile 12 well culture plates (Corning Inc., Cat. No. 3512)

Procedure: Add 0.25 ml of cell suspension into the cell counting chamber and put the cover glass on the top.

Cell counting chamber-Levy Double containing fibroblast cells: Let the cell stabilize and then count the number of cells in the nine big squares under the inverted microscope. The average number of cells (AvC), multiplied by 10, gives the density of cells (DC) expressed in number of cells/mm$^3$. Dilute the cell suspension with M-2 medium to reach the density of 50 cells/mm$^3$ in a total volume of 1.5 ml. Use (1.5 ml)×(50)/AvC for the cell suspension and complete the rest up to 1.5 ml with M-2 medium. Three wells are used for each cell line. Therefore, multiply the numbers in step 3 by 3. Prepare the 4.5 ml mixture in a 15 ml sterile plastic tube and gently homogenize using a 10 ml pipettes. Add 1.5 ml in each of the three wells. Label the three well plates with patient code, date, and passage number. Spray outside of 12 well culture plates with 70% EtOH and place in the incubator.

EXAMPLE 4

Verifying the Initial Cell Density of Human Skin Fibroblast Through Image Analysis Equipment and Materials: Inverted microscope. Image J.

Procedure: After 10 minutes in the incubator take the 12 well culture plate out and put it under the inverted microscope.

Cell counting using image analysis: Under the 4× objective align the center of the well with the center of the viewing field. Change the objective to 10× and take one image in the center plus other four by moving one field of view to the left/right, and up/down. Load the image under ImageJ and go to Process/Noise/Despeckle. Then go to Process/Noise/Binary/MakeBinary. Despeckle the binary image 2-3 times then use Analyze/Analyze Particles for counting the cells. The result is under Summary/Count. Be aware that automatic counting of cells overestimates the manual counting by ~12%. The lower threshold for initial cell density is 45 cell/mm$^3$, which corresponds to a cell number of 190 cells under 10×, and to a fractal dimension of 1.4. The higher threshold for initial cell density is 62 cell/mm$^3$, which corresponds to a cell number of 650 cells under 10×, and to a fractal dimension of 1.62. Any well that has an average number of cells outside the two thresholds is discarded.

EXAMPLE 5

Method 1; Scores

Equipment and Materials: Inverted microscope (Westover Digital AMID Model 2000). Micron 2.0.0 Westover Scientific 2008. Image J Procedure: Pictures taken at 48 hours and after to measure total score based on 8 criteria. Three criteria (1, 4, and 5 see below) are represented quantitatively by the average area per number of aggregates.
  Parameters used for screening:
  Existence of large aggregates.
  2. Attachment of cells to the aggregates.
  3. Evidence of aggregates growing.
  4. Small number of aggregates (<10 on a 10× image).
  5. Large number of aggregates (>10 on a 10× image).
  6. Measurable edges within networks.
  7. Evidence of cell migration.
  8. Closeness to percolation limit (cells form continuous streams).
  Total score: (1) First four parameters are specific to Alzheimer's disease (AD) and score with "−1" if present and with "0" if absent. (2) The last four parameters are specific to age matched controls (AC) and to non Alzheimer's dementias (Non-ADD), and score with "+1" if present and with "0" if absent. (3) Calculate the total score as the sum of all eight values. If total score is positive or zero the cells is AC or Non-ADD. If total score is negative the cells are AD.
  Average area per average number of aggregates: (1) Import images into Micron 2.0.0 and under Measurement/Ellipse Area measure the aggregates one by one. Fit an ellipse on aggregate and area is provided automatically by the software. (2) Collect the areas in a spreadsheet and extract the number of aggregates automatically with the function COUNT. (3) Calculate the average area and the average number of aggregates for each image as well as the ratio of the two. (4) Average the area per # aggregates for all five images for each well. (5) Average the area per # aggregates for all three wells for the same cell line. (6) If area per # aggregates is smaller than 1000 the cell lines are AC or Non-ADD and if it is bigger than 1000 then the cells are AD.

EXAMPLE 6

Method 2; Fractal Analysis

Equipment and Materials: Inverted microscope (Westover Digital AMID Model 2000). Image J. Plug in FracLac.
Procedure: Pictures taken after 48 hours and calculate fractal dimension.
Parameters used for screening: (1) Existence of large aggregates.

EXAMPLE 7

Preparation of Mediums

Preparation of mediums: DMEM (high glucose), Cat. No. 10313-039, Invitrogen Gibco (Store in 4° C. refrigerator); FBS, Cat. No. 10082-147, Invitrogen Gibco (Aliquot 50 ml and store at −20° C.); PS (Penicillin and streptomycin solution) Cat. No. 15140-122, Invitrogen (Aliquot 5 ml and store at −20° C.). M-1 (Medium-1) DMEM with 45% and 1% PS. M-2 (Medium-2) DMEM with 10% and 1% PS. Filter, label and store in 4° C. refrigerator, up to 1 month).

What is claimed:
1. A method of diagnosing Alzheimer's Disease in a human subject comprising the steps of
  (a) obtaining one or more fibroblast cells from a human subject;
  (b) culturing the one or more fibroblast cells for a time period to achieve cell aggregation, wherein the one or more fibroblast cells are cultured in a protein mixture comprising an extracellular matrix preparation chosen from laminin, collagen, heparin sulfate proteoglycans, entactin/nidogen, and/or combinations thereof;
  (c) determining the average area of cell aggregates and dividing the average area by the number of aggregates to obtain the area per number of aggregates;
  (d) comparing the determination of step (c) with the area per number of aggregates determined using non-Alzheimer's Disease cells; and
  (e) diagnosing the presence or absence of Alzheimer's Disease based on the comparison in step (d), wherein the diagnosis is positive for Alzheimer's Disease if the area per number of aggregates determined in step (c) is greater than the area per number of aggregates determined using the non-Alzheimer's Disease cells.
2. The method of claim 1, wherein the diagnosis is confirmed using at least one additional diagnostic step.
3. The method of claim 2, wherein the at least one additional diagnostic step is chosen from performing an integrated score analysis, performing a cell migration analysis, performing a fractal analysis and performing a lacunarity analysis.
4. The method of claim 1, wherein the non-Alzheimer's Disease cells in step (d) are age-matched control (AC) cells.
5. The method of claim 1, wherein the protein mixture further comprises growth factor.
6. The method of claim 1, wherein the extracellular matrix protein is extracted from a tumor.
7. The method of claim 1, wherein the tumor is the EHS mouse sarcoma.
8. A method comprising: (a) culturing a skin cell from a human subject in need of Alzheimer's Disease diagnosis for a time period; (b) measuring cell morphology characteristics associated with a network of fibroblasts of the cell; (c) performing a calculation related to the cell morphology characteristics; and (d) comparing the calculation of step (c) with an independently determined parameter associated with known non-Alzheimer's disease cells; wherein the cell morphology characteristics are selected from the group consisting of: the presence or absence of big clumps, the presence or absence of cells attached to the clumps, the presence or absence of big clumps growing, the number of clumps, the presence or absence of remnant edges from a previously formed network of the clumps, the number of cells migrating, the presence or absence of cells being near percolation; or the group comprising: number of fibroblast clumps, size of fibroblast clumps, growth of fibroblast clumps, and combinations thereof.

9. The method of claim 8, wherein the calculation of step (c) comprises assigning a discrete value for each of the cell morphology characteristics and summing said values.

10. The method of claim 9, wherein the summation is used to diagnose AD or the absence of AD.

11. The method of claim 8, wherein the cell is cultured in a protein mixture.

12. The method of claim 11, wherein the protein mixture comprises an extracellular matrix preparation chosen from laminin, collagen, heparin sulfate proteoglycans, entactin/nidogen, and/or combinations thereof.

13. The method of claim 11, wherein the protein mixture further comprises growth factor.

14. The method of claim 12, wherein the extracellular matrix protein is extracted from a tumor.

15. The method of claim 14, wherein the tumor is the EHS mouse sarcoma.

16. A method of diagnosing Alzheimer's Disease in a subject comprising the steps of (a) obtaining one or more cells from the subject and growing said one or more cells in a tissue culture medium; (b) determining an integrated score based on one or more characteristics of the cultured cells; (c) comparing the integrated score to an integrated score determined for non-Alzheimer's Disease cells; (d) diagnosing the presence or absence of Alzheimer's Disease in the subject; wherein the one or more characteristics used to calculate the integrated score are selected from the group consisting of cell aggregate size, attachment of cells to aggregates, evidence of cell aggregate growth, number of cell aggregates, edges within networks, evidence of cell migration and closeness to percolation limit or cell density.

17. The method of claim 16, wherein the diagnosis is confirmed using one or more additional diagnostic methods.

18. The method of claim 17, wherein the one or more additional diagnostic methods are selected from the group consisting of methods comprising determining an integrated score, methods comprising calculating area per number of aggregates, methods comprising cell migration analysis, methods comprising fractal analysis and methods comprising lacunarity analysis.

19. A method of determining Alzheimer's Disease duration in a subject comprising (a) obtaining one or more cells from the subject; (b) measuring cell migration characteristics or average area per number of cell aggregates for known AD cell lines; (c) preparing standard curves using the data obtained in step (b); (d) measuring migration characteristics or average area per number of cell aggregates obtained in step (a) and (e) determining AD disease duration in the subject.

20. The method of claim 19, wherein the cells are fibroblasts.

21. The method of claim 19, wherein subjects identified as having AD for 10 years or less are identified as having increased responsiveness to treatment of AD.

22. The method of claim 19, wherein subjects identified as having AD for 9 years or less are identified as having increased responsiveness to treatment of AD.

23. The method of claim 19, wherein subjects identified as having AD for 8 years or less are identified as having increased responsiveness to treatment of AD.

24. The method of claim 19, wherein subjects identified as having AD for 7 years or less are identified as having increased responsiveness to treatment of AD.

25. The method of claim 19, wherein subjects identified as having AD for 6 years or less are identified as having increased responsiveness to treatment of AD.

26. The method of claim 19, wherein subjects identified as having AD for 5 years or less are identified as having increased responsiveness to treatment of AD.

27. The method of claim 19, wherein subjects identified as having AD for 4 years or less are identified as having increased responsiveness to treatment of AD.

28. The method of claim 19, wherein subjects identified as having AD for 3 years or less are identified as having increased responsiveness to treatment of AD.

29. The method of claim 19, wherein subjects identified as having AD for 2 years or less are identified as having increased responsiveness to treatment of AD.

30. The method of claim 19, wherein subjects identified as having AD for 1 years or less are identified as having increased responsiveness to treatment of AD.

* * * * *

UNITED STATES PATENT AND TRADEMARK OFFICE
CERTIFICATE OF CORRECTION

| | | |
|---|---|---|
| PATENT NO. | : 8,658,134 B2 | |
| APPLICATION NO. | : 12/896862 | |
| DATED | : February 25, 2014 | |
| INVENTOR(S) | : Florin Valentin Chirila et al. | |

It is certified that error appears in the above-identified patent and that said Letters Patent is hereby corrected as shown below:

In the Claims

In claim 7, column 20, line 52, "claim 1," should read --claim 6,--.

Signed and Sealed this
Third Day of June, 2014

Michelle K. Lee
*Deputy Director of the United States Patent and Trademark Office*